US012673951B2

(12) United States Patent
Cai et al.

(10) Patent No.: US 12,673,951 B2

(45) Date of Patent: Jul. 7, 2026

(54) SUBSTITUTED PYRAZOLOQUINAZOLINONE COMPOUNDS AND APPLICATION THEREOF

(71) Applicant: IMPACT THERAPEUTICS (SHANGHAI), INC, Shanghai (CN)

(72) Inventors: Sui Xiong Cai, Shanghai (CN); Ye Edward Tian, Shanghai (CN); Xiaozhu Wang, Nanjing (CN)

(73) Assignee: Impact Therapeutics (Shanghai) Inc, Shanghai (CN)

(*) Notice: Subject to any disclaimer, the term of this patent is extended or adjusted under 35 U.S.C. 154(b) by 1096 days.

(21) Appl. No.: 17/626,029

(22) PCT Filed: Jul. 8, 2020

(86) PCT No.: PCT/CN2020/100869

§ 371 (c)(1),
(2) Date: Jan. 10, 2022

(87) PCT Pub. No.: WO2021/004482

PCT Pub. Date: Jan. 14, 2021

(65) Prior Publication Data

US 2022/0259211 A1 Aug. 18, 2022

(30) Foreign Application Priority Data

Jul. 10, 2019 (CN) ......................... 201910628148.2

(51) Int. Cl.
*C07D 487/04* (2006.01)
*A61K 31/519* (2006.01)
*A61K 45/06* (2006.01)
*A61P 35/00* (2006.01)

(52) U.S. Cl.
CPC .......... *C07D 487/04* (2013.01); *A61K 31/519* (2013.01); *A61K 45/06* (2013.01); *A61P 35/00* (2018.01)

(58) Field of Classification Search
CPC ........ A61P 35/00; A61P 35/02; C07D 487/04; A61K 31/519
See application file for complete search history.

(56) References Cited

U.S. PATENT DOCUMENTS 10,874,670 B2 12/2020 Cai et al.
2022/0354859 A1 11/2022 Cai et al.

FOREIGN PATENT DOCUMENTS

CN 102399218 A 4/2012
WO WO-2012034526 A1 3/2012
WO WO-2015170081 A1 * 11/2015 ........... A61K 31/444
WO WO-2018127195 A1 * 7/2018 ......... A61K 31/4985
WO WO-2018153365 A1 8/2018

OTHER PUBLICATIONS

Hemdan "Synthesis and antimicrobial assessments of some quinazolines and their annulated systems" J. Chem. Res. 2017 41 106-111 (Year: 2017).*

Herskovic "Combined Chemotherapy and Radiotherapy Compared with Radiotherapy Alone in Patients with Cancer of the Esophagus" New England Journal of Medicine 1992 326 24 1593-1598 (Year: 1992).*

Bakkenist, C., and Kastan, M. B., "DNA damage activates ATM through intermolecular autophosphorylation and dimer dissociation," Nature 421(6922):499-506, Nature Publishing Group, United Kingdom (Jan. 2003).

Choi, M., et al., "ATM Mutations in Cancer: Therapeutic Implications," Mol Cancer Ther 15(8):1781-1791, American Association for Cancer Research, United States (Aug. 2016).

Cremona, C. A., et al., "Extensive DNA damage-induced sumoylation contributes to replication and repair and acts in addition to the mecl checkpoint," Mol Cell 45(3):422-432, Cell Press, United Kingdom (Feb. 2012).

Cremona, C. A., and Behrens, A., "ATM signaling and cancer," Oncogene 33(26):3351-3360, Nature Publishing Group, United Kingdom (Jun. 2014).

Degorce, S. L., et al., "Discovery of Novel 3-Quinoline Carboxamides as Potent, Selective, and Orally Bioavailable Inhibitors of Ataxia Telangiectasia Mutated (ATM) Kinase," J Med Chem 59(13):6281-6292, American Chemical Society, United States (Jul. 2016).

Gilardini Montani, M. S., et al., "ATM-depletion in breast cancer cells confers sensitivity to PARP inhibition," J Exp Clin Cancer Res 32(1):95, BioMed Central Ltd., United Kingdom (Nov. 2013).

International Search Report and Written Opinion for International Application No. PCT/CN2020/100869, mailed on Oct. 10, 2020, China National Intellectual Property Administration, China, 12 pages.

Kubota, E., et al., "Low ATM protein expression and depletion of p53 correlates with olaparib sensitivity in gastric cancer cell lines," Cell Cycle 13(13):2129-2137, Landes Bioscience, United States (Jul. 2014).

(Continued)

*Primary Examiner* — Andrew D Kosar
(74) *Attorney, Agent, or Firm* — Sterne, Kessler, Goldstein & Fox P.L.L.C.

(57) ABSTRACT

A compound of formula I, or a stereoisomer, tautomer, N-oxide, hydrate, isotope-substituted derivative, or solvate thereof, or a pharmacologically acceptable salt thereof, or a mixture thereof, of a prodrug thereof. The compound of formula I is a kinase inhibitor which can be used for treating clinical disorder caused by DDR deficiencies, such as cancers.

I

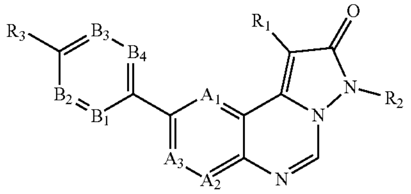

20 Claims, No Drawings

(56) References Cited

OTHER PUBLICATIONS

Toledo-Sherman, S., et al., "Optimization of Potent and Selective Ataxia Telangiectasia-Mutated Inhibitors Suitable for a Proof-of-Concept Study in Huntington's Disease Models," J Med Chem 62(6):2988-3008, American Chemical Society, United States (Mar. 2019).

Weber, A. M., and Ryan, A. J., "ATM and ATR as therapeutic targets in cancer," Pharmacol Ther 149:124-138, Elsevier, Netherlands (May 2015).

Weber, A. M., et al., "Phenotypic consequences of somatic mutations in the ataxia-telangiectasia mutated gene in non-small cell lung cancer," Oncotarget 7(38):60807-60822, Impact Journals LLC, United States (Sep. 2016).

* cited by examiner

SUBSTITUTED PYRAZOLOQUINAZOLINONE COMPOUNDS AND APPLICATION THEREOF

FIELD OF THE DISCLOSURE

This disclosure is in the field of medicinal chemistry. In particular, the disclosure relates to substituted pyrazolo[1, 5-c]quinazolin-2(3H)-one compounds and related compounds, and the use of these compounds as kinase inhibitors, including ATM protein kinase inhibitors and application of anti-cancer drugs.

RELATED ART

Mammalian cells encounter many external and internal challenges that cause DNA damage every day, including mutations in DNA bases. These mutations cause changes in cell function, including the occurrence of malignant tumors, even directly cause cell death. Therefore, mammalian cells have evolved a sophisticated DNA damage response (DDR) mechanism to address these challenges. This mechanism detects and repairs DNA damage by short cell cycle pauses to ensure genome stability and cell survival.

The occurrence of DDR and cancer has an inextricable relationship. Scientific research has found that deficiencies in DDR repair mechanisms can lead to cancer at multiple levels, such as base mutations in the DDR gene have been found to cause a variety of cancers, including breast cancer and ovarian cancer in women with mutations in the BRCA1 or BRCA2 gene, which are much higher than in people without mutations. BRCA1 and BRCA2 are important components of DDR to repair DNA double-strand breaks based on homologous recombination. Studies have also found deletions or loss of function of key proteins in DDR cells of various malignant tumors or regulate the cell cycle, including p53, ATM, ATR, BRCA1/2 and so on.

In recent years, with the development of science and understanding of the mechanism of cell DDR, there has been great interest in the development of novel anticancer targeted therapeutic drugs for the mutation and loss of function of DDR constituent proteins. For example, PARP inhibitors can specifically kill cancer cells with BRCA1/2 mutations by inhibiting the single-strand repair mechanism of DNA damage. This mechanism of action is called synthetic lethality.

ATM kinase is one of the important constituent proteins of DDR and belongs to the PI3K related serine/threonine kinase family. ATM kinase gene was cloned when the telangiectasia ataxia syndrome was studied in 1995. ATM gene is located on human chromosome 11q22-23 and is a coding sequence comprising 66 exons and 9168 bases. ATM kinase is a large protein with a molecular weight of approximately 350 kDa. ATM kinase is one of the important components of DDR. ATM kinase is activated when DNA damage causes double-strand breaks. Its function is to achieve cell cycle transition point pause by phosphorylation of downstream proteins, repairing damaged DNA by homologous recombination or entering apoptotic mechanism (Weber and Ryan, 2016).

ATM kinase signal transduction can be roughly divided into two mechanisms: the typical mechanism is activated by DNA double-strand breaks. When DNA double-strand breaks are detected, the ATM kinase is transported to the breaking site and activated. Although the detailed activation mechanism is not well understood, the activation process includes from homodimers into active monomers (Bakkenist et al., 2003), self-phosphorylation of Ser1981 site and other sites, and acetylation. Activated ATM kinase further phosphorylates downstream substrates, including cell cycle checkpoint proteins (such as Chk1 and Chk2), DNA repair proteins (BRCA1 and RAD51), or apoptotic pathway proteins (p53). Studies have shown that there are more than 700 proteins phosphorylated after DNA double-strand breaks (Choi, Kipps and Kurzrock, 2016). In addition, ATM is involved in functions that are not directly related to DNA damage, such as metabolism, stress, etc. These functions are often referred to as atypical mechanisms (Cremona et al., 2013).

The development of new anticancer drugs targeting ATM kinase mainly depends on two considerations. Radiotherapy or cytotoxic chemotherapeutics, such as topoisomerase inhibitors and DNA methylation drugs, etc., which are usually toxic to rapidly differentiated cancer cells based on DNA damage, are greatly reduced in cytotoxicity due to the presence of DDR. Therefore, ATM inhibitors, combined with inhibitors that inhibit the function of DDR constituent proteins, such as PARP inhibitors, can greatly enhance the efficacy of these drugs. Studies by Gilardini Montani M S et al. (J Exp Clin Cancer Res, 2013, 32:95) have shown that reducing ATM expression could enhance the sensitivity of breast cancer cells to PARP inhibitors, which provided a theoretical basis for the possibility of combination of ATM inhibitors and PARP inhibitors in the treatment of breast cancer. In addition, Kubota E et al. (Cell Cycle, 2014, 13 (13): 2129-2137) found that the expression of ATM protein in gastric cancer cells was significantly correlated with the sensitivity of PARP inhibitor olaparib. ATM inhibitors enhance the sensitivity of p53-inactivated gastric cancer cells to olaparib. Therefore, the combined use of ATM inhibitors and PARP inhibitors may be used to treat gastric cancer. In addition, for cancer cells with DDR deficiency, ATM kinase inhibitors can be used alone by synthesizing lethal mechanism and targeted anticancer drugs can be developed for specific patients, which have the characteristics of good efficacy and low toxicity.

Degorce S L et al. (J Med Chem, 2016, 59: 6281-6292) reported a series of 3-quinolinformamides as ATM kinase inhibitors, and observed good efficacy of ATM kinase inhibitors combined with irinotecan in animal model.

Genetic and pharmacological evidence indicates that the reduction of ataxia telangiectasia-mutated (ATM) kinase activity can ameliorate mutant huntingtin (mHTT) toxicity in cellular and animal models of Huntington's disease (HD), suggesting that selective inhibition of ATM could provide a novel clinical intervention to treat HD. Leticia T S et al. (I Med Chem, 2019, 62: 2988-3008) reported brain-penetrant ATM inhibitors that have robust pharmacodynamic (PD) effects consistent with ATM kinase inhibition in the mouse brain and an understandable pharmacokinetic/PD (PK/PD) relationship.

WO2012034526 disclosed fused heteroaromatic compounds as PI3K kinase inhibitors, wherein, $A^1$ is N or CH; $A^4$ and $A^5$ are independently N or $CR^2$, $R^2$ is independently selected from H, alkyl, alkenyl, alkynyl, aryl and so on; $A^2$ and $A^3$, together with B ring form a 5-membered heteroaryl or heterocycle containing 1 to 4 heteroatoms selected from N, O, and S; $\overset{\cdots}{=}$ is a single bond or a double bond; $R^1$ is heteroaryl.

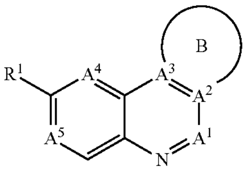

WO2015170081 disclosed imidazolidoquinolones as ATM kinase inhibitors, wherein, Q is cyclobutyl or cyclopentyl or oxetanyl, tetrahydrofuranyl or oxanyl; $R^1$ is methyl; $R^2$ is H or methyl; or $R^1$ and $R^2$ together form an azetidinyl, pyrrolidinyl or piperidinyl; $R^3$ is H or fluoro; $R^4$ is H or methyl; and $R^5$ is H or fluoro.

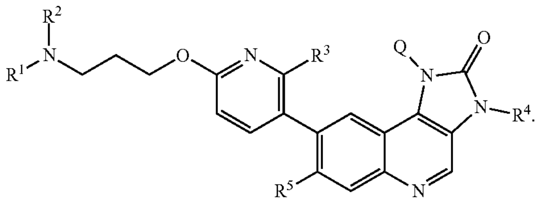

WO2018127195 and WO2018153365 disclosed substituted fused heteroaromatic compounds as ATM kinase inhibitors.

SUMMARY OF THE DISCLOSURE

The disclosure provides novel substituted fused heteroaromatic compounds, as represented in Formulae I, IIa, IIb and III as kinase inhibitors, especially ATM kinase inhibitors.

The present disclosure also provides pharmaceutical compositions comprising a compound of Formula I, IIa, IIb or III in an effective amount for the treatment of cancer.

In a concrete embodiment, the pharmaceutical composition useful for the treatment of cancer may also contain one or more pharmaceutically acceptable carriers or diluents.

In a concrete embodiment, the pharmaceutical composition useful for the treatment of cancer may also contain at least one known anticancer drugs or its pharmaceutically acceptable salts.

The disclosure is also directed to methods for the preparation of novel compounds of Formulae I, IIa, IIb and III.

DETAILED DESCRIPTION OF THE DISCLOSURE

The disclosure finds novel substituted fused heteroaromatic compounds as kinase inhibitors, especially ATM kinase inhibitors, as represented in Formula I.

It should be understood that the characteristics of the embodiments described herein can be arbitrarily combined to form the technical solution of this disclosure. The definitions of each group herein shall apply to any of the embodiments described herein. For example, the definitions of substituents for alkyl groups herein shall apply to any of the embodiments described herein unless the substituents for alkyl groups are clearly defined in the embodiment.

Specifically, compounds of the present disclosure are represented by Formula I:

I

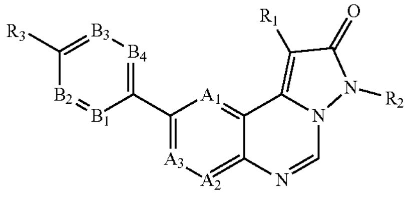

or stereoisomers, tautomers, N-oxides, hydrates, isotope-substituted derivatives, solvates or pharmaceutically acceptable salts thereof, or mixtures thereof, or prodrugs, wherein:

$A_1$, $A_2$ and $A_3$ each are independently N or $CR_4$, $CR_5$, $CR_6$;

$B_1$, $B_2$, $B_3$ and $B_4$ each are independently N or $CR_7$, $CR_8$, $CR_9$, $CR_{10}$;

$R_1$ is optionally substituted alkyl, optionally substituted alkoxy, optionally substituted amino, optionally substituted carbocyclic group, optionally substituted heterocyclic group, optionally substituted aryl or optionally substituted heteroaryl;

$R_2$ is H or optionally substituted alkyl;

$R_3$ is H, alkoxy, amino, carbocyclic group, heterocyclic group, aryl or heteroaryl; wherein, the said alkoxy, amino, carbocyclic group, heterocyclic group, aryl and heteroaryl may be optionally substituted.

$R_4$-$R_{10}$ each are independently H, halogen, alkyl, alkoxy, alkenyl, alkynyl, amino (amido), nitro, cyano, acyloxy, hydroxyl, mercapto, alkylthio, azide or carboxyl; wherein, the said alkyl, alkoxy, alkenyl, alkynyl, amino (amido) nitro, cyano, acyloxy, hydroxyl, mercapto, alkylthio, azide or carboxyl may be optionally substituted.

In one or more of the foregoing embodiment, in compound of Formula I, $A_1$, $A_2$ and $A_3$ each are independently $CR_4$, $CR_5$ and $CR_6$; wherein, $R_4$-$R_6$ each are independently H, halogen, $C_1$-$C_4$ alkyl, $C_1$-$C_4$ alkoxy or halo $C_1$-$C_4$ alkyl. Preferably, $R_4$ and $R_5$ each are independently H or $C_1$-$C_4$ alkyl, more preferably H. Preferably, $R_6$ is H, halogen or $C_1$-$C_4$ alkoxy.

In one or more of the foregoing embodiment, in compound of Formula I, $R_2$ is $C_1$-$C_{10}$ alkyl, preferably $C_1$-$C_6$ alkyl; more preferably, $R_2$ is methyl.

In one or more of the foregoing embodiments, in compound of Formula I, when substituted, the substituent on $R_1$ is selected from halogen, hydroxy, $C_{1-6}$ alkyl, $C_{1-6}$ alkoxy and halo $C_{1-6}$ alkyl, preferably $C_{1-6}$ alkyl; wherein, the number of substituent is 1-4. Preferably, when $R_1$ is 6-membered heteroaryl or heterocyclic group, such as, morpholinyl, piperazinyl or piperidinyl, the position of the substituent is meta and/or para; the number of substituent can be 2 or 3. For example, $R_1$ can be a heterocyclic group substituted by two or three $C_{1-4}$ alkyl in the meta and para positions.

In one or more of the foregoing embodiments, in compound of Formula I, $R_1$ is optionally substituted $C_{1-6}$ alkyl, heterocyclic group or heteroaryl optionally substituted by 1-4 $C_{1-6}$ alkyl; preferably, $R_1$ is selected from $C_{1-4}$ alkyl, tetrahydropyranyl optionally substituted by 1-4 $C_{1-6}$ alkyl, piperidinyl optionally substituted by 1-4 $C_{1-6}$ alkyl, morpholinyl optionally substituted by 1-4 $C_{1-6}$ alkyl, piperazinyl optionally substituted by 1-4 $C_{1-6}$ alkyl. In some embodiments, $R_1$ is selected from isopropyl, tetrahydropyranyl, piperidinyl, morpholinyl optionally substituted by 1-2 $C_{1-4}$ alkyl and piperazinyl optionally substituted by 1-3 $C_{1-4}$ alkyl. Preferably, $R_1$ is optionally substituted $C_{1-6}$ alkyl and heterocyclic group optionally substituted by 1-3 $C_{1-4}$ alkyl, including:

, 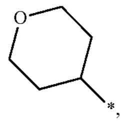, 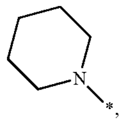, 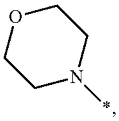, 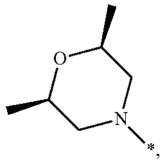, 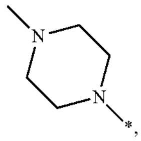, 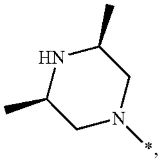, 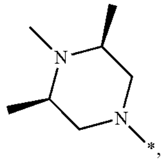, and 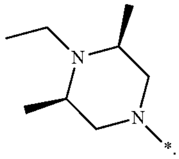.

In one or more of the foregoing embodiments, in compound of Formula I, the ring containing $B_1$-$B_4$ is an optionally substituted pyridyl or an optionally substituted phenyl. Preferably, The ring containing $B_1$-$B_4$ is an optionally substituted phenyl or an optionally substituted pyridyl where $B_2$ is N. The said substituents can be as defined in $R_7$-$R_{10}$.

In one or more of the foregoing embodiments, in compound of Formula I, $R_7$-$R_{10}$ each are independently H, $C_{1-6}$ alkyl, halogen and halo $C_{1-6}$ alkyl; preferably, $R_7$-$R_{10}$ each are independently halogen and halo $C_{1-4}$ alkyl.

In one or more of the foregoing embodiments, in compound of Formula I, $B_2$ is N or $CR_8$, wherein, $R_8$ is H, halogen, $C_{1-4}$ alkyl or halo $C_{1-4}$ alkyl. In some embodiments, $B_1$ is CH, $B_2$ is N, $B_3$ is CH, $B_4$ is CH. In some embodiments, $B_1$ is CH, $B_2$ is $CR_8$, $B_3$ is CH, $B_4$ is CH, wherein, $R_8$ is H, halogen, $C_{1-4}$ alkyl or halo $C_{1-4}$ alkyl.

In one or more of the foregoing embodiments, in compound of Formula I, $R_3$ is optionally substituted $C_{1-6}$ alkoxy or optionally substituted heterocyclic group. The number of substituents can be 1-2, preferably 1.

In one or more of the foregoing embodiments, in compound of Formula I, when substituted, the substituent on $R_3$ is selected from —$NR_{11}R_{12}$, wherein, $R_{11}$ and $R_{12}$ each are independently H or $C_{1-6}$ alkyl; or $R_{11}$ and $R_{12}$ together with N form an optionally substituted 4-8 membered heterocyclic group, preferably a 5-8 membered heterocyclic group, such as piperidinyl; preferably, when substituted, the substituents of the heterocyclic group are 1-2 $C_{1-4}$ alkyl.

In one or more of the foregoing embodiments, in compound of Formula I, $R_3$ is selected from H, $C_{1-6}$ alkoxy optionally substituted by —$NR_{11}R_{12}$ or heterocyclic group (such as piperidinyl) optionally substituted by —$NR_{11}R_{12}$; wherein, $R_{11}$ and $R_{12}$ each are independently H and $C_{1-6}$ alkyl. Preferably, $R_3$ is selected from:

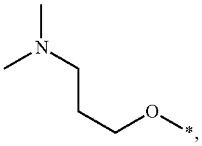, 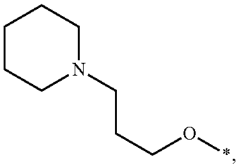, 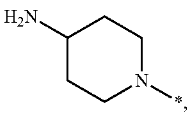, 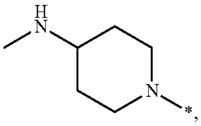, 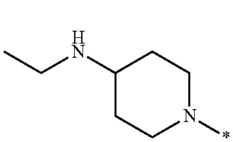 and 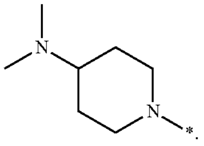.

Preferred compounds of the present disclosure are represented by Formulae IIa and IIb:

IIa

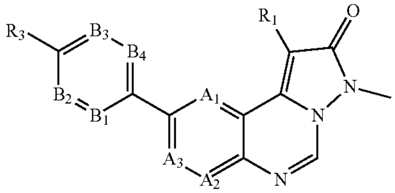

IIb

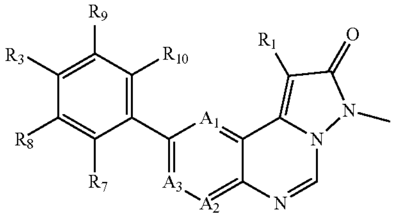

or stereoisomers, tautomers, N-oxides, hydrates, isotope-substituted derivatives, solvates or pharmaceutically acceptable salts thereof, or mixtures thereof, or prodrugs, wherein:

$A_1$-$A_3$, $B_1$, $B_3$-$B_4$, $R_1$, $R_3$ and $R_7$-$R_{10}$ are defined as that in Formula I.

In one or more of the foregoing embodiments, in compound of Formulae Ha and IIb, $A_1$-$A_3$, $B_1$, $B_3$-$B_4$, $R_1$, $R_3$ and $R_7$-$R_{10}$ are defined as in any one of the embodiment of Formula I as described above.

In one or more of the foregoing embodiments, in compound of Formula IIa or IIb, $A_1$, $A_2$ and $A_3$ each are independently $CR_4$, $CR_5$, and $CR_6$; wherein, $R_4$-$R_6$ each are independently H, halogen, $C_1$-$C_4$ alkyl, $C_1$-$C_4$ alkoxy or halo $C_1$-$C_4$ alkyl. Preferably, $R_4$ and $R_5$ each are independently H or $C_1$-$C_4$ alkyl, more preferably H. Preferably, $R_6$ is H, halogen or $C_1$-$C_4$ alkoxy.

In one or more of the foregoing embodiments, in compound of Formula IIa, $B_1$, $B_3$ and $B_4$ each are independently $CR_7$, $CR_9$ and $CR_{10}$; $R_7$, $R_9$ and $R_{10}$ each are independently H, halogen, $C_1$-$C_4$ alkyl or halo $C_1$-$C_4$ alkyl.

In one or more of the foregoing embodiments, in compound of Formula IIb, $R_8$ is H, halogen, $C_{1-4}$ alkyl or halo $C_{1-4}$ alkyl. Preferably, $R_8$ is halogen and halo $C_{1-4}$ alkyl. Preferably, $R_7$, $R_9$ and $R_{10}$ each are independently H, halogen, $C_1$-$C_4$ alkyl or halo $C_1$-$C_4$ alkyl; more preferably H.

In one or more of the foregoing embodiments, in compound of Formula IIa or IIb, $R_1$ is optionally substituted $C_{1-6}$ alkyl, heterocyclic group or heteroaryl optionally substituted by 1-4 $C_{1-6}$ alkyl; preferably, $R_1$ is selected from $C_{1-4}$ alkyl, tetrahydropyranyl optionally substituted by 1-4 $C_{1-6}$ alkyl, piperidinyl optionally substituted by 1-4 $C_{1-6}$ alkyl, morpholinyl optionally substituted by 1-4 $C_{1-6}$ alkyl, piperazinyl optionally substituted by 1-4 $C_{1-6}$ alkyl. In some embodiments, $R_1$ is selected from isopropyl, tetrahydropyranyl, piperidinyl, morpholinyl optionally substituted by 1-2 $C_{1-4}$ alkyl and piperazinyl optionally substituted by 1-3 $C_{1-4}$ alkyl. Preferably, $R_1$ is optionally substituted $C_{1-6}$ alkyl and heterocyclic group optionally substituted by 1-3 $C_{1-4}$ alkyl, including:

,
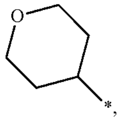,
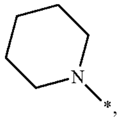,
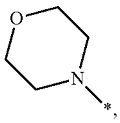,
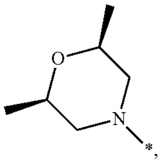,
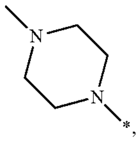,
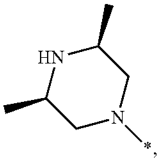,
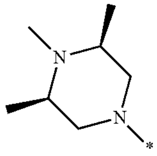 and
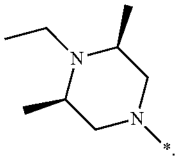.

In one or more of the foregoing embodiments, in compound of Formula IIa, the ring containing $B_1$, $B_3$-$B_4$ is an optionally substituted pyridyl. It should be understood that, in addition to $R_3$, the substituents on the ring containing $B_1$, $B_3$-$B_4$ may also include $R_7$, $R_9$ and $R_{10}$. Preferably, $R_7$, $R_9$ and $R_{10}$ each are independently halogen, $C_1$-$C_4$ alkyl or halo $C_1$-$C_4$ alkyl.

In one or more of the foregoing embodiments, in compound of Formula IIa or IIb, $R_3$ is selected optionally substituted $C_{1-6}$ alkoxy and optionally substituted heterocyclic group. The number of substituents can be 1-2, preferably 1. Preferred substituents include —$NR_{11}R_{12}$, wherein, $R_{11}$ and $R_{12}$ each are independently H or $C_{1-6}$ alkyl; or $R_{11}$ and $R_{12}$ together with N form an optionally substituted 4-8 membered heterocyclic group, preferably a 5-8 membered heterocyclic group, such as piperidinyl; preferably, when substituted, the substituents on the heterocyclic group are 1-2 $C_{1-4}$ alkyl.

In one or more of the foregoing embodiments, in compound of Formula IIa or IIb, $R_3$ is selected from H, $C_{1-6}$ alkoxy optionally substituted by —$NR_{11}R_{12}$ or heterocyclic group (piperidinyl) optionally substituted by —$NR_{11}R_{12}$; wherein, $R_{11}$ and $R_{12}$ each are independently H and $C_{1-6}$ alkyl; or $R_{11}$ and $R_{12}$ together with N form an optionally substituted 4-8 membered heterocyclic group, preferably a 5-8 membered heterocyclic group, such as piperidinyl; preferably, when substituted, the substituents on the heterocyclic group are 1-2 $C_{1-4}$ alkyl. Preferably, $R_3$ includes:

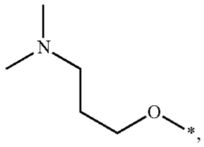,
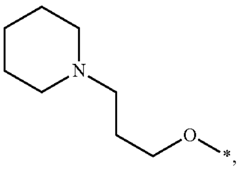,
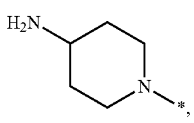,
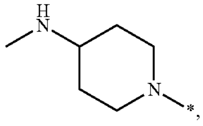,
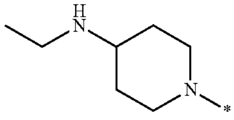 and
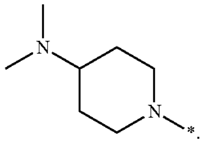.

In one or more of the foregoing embodiments, in compound of Formulae I, IIa and IIb, the said optionally substituted alkyl, alkoxy, amino, carbocyclic, heterocyclic, aryl or heteroaryl of $R_1$ can be substituted by one or more substitutents selected from the group, of alkyl, alkoxy, amino, carbocyclic, heterocyclic, aryl or heteroaryl.

In one or more of the foregoing embodiments, in compound of Formulae I, IIa and IIb, the said optionally substituted alkoxy, amino, carbocyclic, heterocyclic, aryl or heteroaryl of $R_3$ can be substituted by one or more substitutents selected from the group of alkoxy, amino, carbocyclic, heterocyclic, aryl or heteroaryl.

In one or more of the foregoing embodiments, in compound of Formulae I, IIa and IIb, the said optionally substituted alkyl, alkoxy, alkenyl, alkynyl, amino (amido), acyloxy, hydroxyl, mercapto, alkylthio, or carboxyl of $R_4$-$R_{10}$ can be substituted by one or more substitutents selected from the group of alkyl, alkoxy, alkenyl, alkynyl, amino (amido), acyloxy, hydroxyl, mercapto, alkylthio, or carboxyl.

In one or more of the foregoing embodiments, in compound of Formula IIb, the said optionally substituted alkyl, alkoxy, alkenyl, alkynyl, amino-(amido), acyloxy, hydroxyl, mercapto, alkylthio, or carboxyl of $R_7$-$R_{10}$ can be substituted by one or more substitutents selected from the group of alkyl, alkoxy, alkenyl, alkynyl, amino (amido), acyloxy, hydroxyl, mercapto, alkylthio, or carboxyl.

In one or more of the foregoing embodiments, in compound of Formulae I, IIa and IIb, $A_1$, $A_2$ and $A_3$ each are independently $CR_4$, $CR_5$ and $CR_6$; wherein, $R_4$-$R_6$ each are independently H, halogen, $C_1$-$C_4$ alkyl, $C_1$-$C_4$ alkoxy or halo $C_1$-$C_4$ alkyl, preferably H, halogen and $C_1$-$C_4$ alkyl. The ring containing $B_1$-$B_4$ (Formula I) or $B_1$, $B_3$-$B_4$ (Formula II) is an optionally substituted pyridyl or an optionally substituted phenyl, wherein, $R_7$-$R_{10}$ each are independently H, $C_1$-$C_6$ alkyl, halogen and halo $C_1$-$C_6$ alkyl, preferably halogen and halo $C_1$-$C_4$ alkyl. $R_1$ is optionally substituted $C_{1-6}$ alkyl, heterocyclic group or heteroaryl optionally substituted by 1-4 $C_{1-6}$ alkyl; preferably, $R_1$ is selected from $C_{1-4}$ alkyl, tetrahydropyranyl optionally substituted by 1-4 $C_{1-6}$ alkyl, piperidinyl optionally substituted by 1-4 $C_{1-6}$ alkyl. $R_2$ is $C_1$-$C_6$ alkyl, preferably methyl. $R_3$ is selected from H, $C_{1-6}$ alkoxy optionally substituted by —$NR_{11}R_{12}$ or heterocyclic group optionally substituted by —$NR_{11}R_{12}$; wherein, $R_{11}$ and $R_{12}$ each are independently H and $C_{1-6}$ alkyl, or $R_{11}$ and $R_{12}$ together with N form an optionally substituted 4-8 membered heterocyclic group, preferably a 5-8 membered heterocyclic group, such as piperidinyl.

In one or more embodiments of the compound of Formula I, compounds of the present disclosure are represented by Formula III:

III

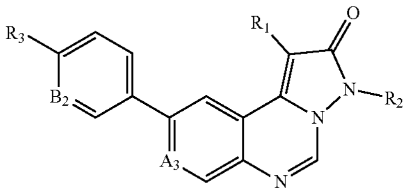

wherein, $B_2$ is $CR_8$, wherein, $R_8$ is halogen or halo $C_{1-4}$ alkyl; $A_3$ is CH; $R_1$ is heterocyclic group (such as tetrahydropyranyl) or $C_{1-4}$ alkyl; $R_2$ is $C_{1-4}$ alkyl; $R_3$ is $C_{1-6}$ alkoxy substituted by —$NR_{11}R_{12}$ or piperidinyl, wherein, $R_{11}$ and $R_{12}$ each are independently H and $C_{1-4}$ alkyl, or $R_{11}$ and $R_{12}$ together with N form a 4-8 membered heterocyclic group optionally substituted by 1-2 $C_{1-4}$ alkyl; or $B_2$ is $CR_8$, wherein, $R_8$ is halogen or halo $C_{1-4}$ alkyl; $A_3$ is CH; $R_1$ is tetrahydropyranyl; $R_2$ is $C_{1-4}$ alkyl; $R_3$ is $C_{1-6}$ alkoxy substituted by —$NR_{11}R_{12}$ or piperidinyl, wherein, $R_{11}$ $_{and}$ $_{R}12$ each are independently H and $C_{1-4}$ alkyl; or $B_2$ is $CR_8$, wherein, $R_8$ is halogen or halo $C_{1-4}$ alkyl; $A_3$ is CH; $R_1$ is $C_{1-4}$ alkyl; $R_2$ is $C_{1-4}$ alkyl; $R_3$ is $C_{1-6}$ alkoxy substituted by —$NR_{11}R_{12}$ or piperidinyl, wherein, $R_{11}$ and $R_{12}$ each are independently H and $C_{1-4}$ alkyl, or $R_{11}$ and $R_{12}$ together with N form a 4-8 membered heterocyclic group (such as piperidinyl) optionally substituted by 1-2 $C_{1-4}$ alkyl; or $B_2$ is N; $A_3$ is $CR_6$; $R_1$ is $C_{1-4}$ alkyl; $R_2$ is heterocyclic group or $C_{1-4}$ alkyl; $R_3$ is $C_{1-6}$ alkoxy substituted by —$NR_{11}R_{12}$ or piperidinyl, wherein, $R_6$ is H or halogen; $R_{11}$ and $R_{12}$ each are independently H and $C_{1-4}$ alkyl, or $R_{11}$ and $R_{12}$ together with N form a 4-8 membered heterocyclic group optionally substituted by 1-2 $C_{1-4}$ alkyl.

In one or more of the foregoing embodiments, preferred compounds of Formulae I, IIa, IIb and III include, without limitation:

9-(6-(3-(dimethylamino)propoxy)pyridin-3-yl)-1-(tetrahydro-2H-pyran-4-yl)pyrazolo[1,5-c]quinazolin-2(3H)-one (Example 1);

9-(6-(3-(dimethylamino)propoxy)pyridin-3-yl)-3-methyl-1-(tetrahydro-2H-pyran-4-yl)pyrazolo[1,5-c]quinazolin-2(3H)-one (Example 2);

9-(6-(3-(piperidin-1-yl)propoxy)pyridin-3-yl)-3-methyl-1-(tetrahydro-2H-pyran-4-yl)pyrazolo[1,5-c]quinazolin-2(3H)-one (Example 3);

9-(6-(3-(dimethylamino)propoxy)pyridin-3-yl)-8-fluoro-3-methyl-1-(tetrahydro-2H-pyran-4-yl)pyrazolo[1,5-c]quinazolin-2(3H)-one (Example 4);

9-(4-(3-(dimethylamino)propoxy)-3-(trifluoromethyl)phenyl)-3-methyl-1-(tetrahydro-2H-pyran-4-yl)pyrazolo[1,5-c]quinazolin-2(3H)-one (Example 5);

9-(4-(4-(dimethylamino)piperidin-1-yl)-3-fluorophenyl)-3-methyl-1-(tetrahydro-2H-pyran-4-yl)pyrazolo[1,5-c]quinazolin-2(3H)-one (Example 6);

9-(3-chloro-4-(4-(dimethylamino)piperidin-1-yl)phenyl)-3-methyl-1-(tetrahydro-2H-pyran-4-yl)pyrazolo[1,5-c]quinazolin-2(3H)-one (Example 7);

9-(4-(4-(dimethylamino)piperidin-1-yl)-3-(trifluoromethyl)phenyl)-3-methyl-1-(tetrahydro-2H-pyran-4-yl)pyrazolo[1,5-c]quinazolin-2(3H)-one (Example 8);

9-(4-(4-aminopiperidin-1-yl)-3-(trifluoromethyl)phenyl)-3-methyl-1-(tetrahydro-2H-pyran-4-yl)pyrazolo[1,5-c]quinazolin-2(3H)-one (Example 9);

9-(4-(4-(methylamino)piperidin-1-yl)-3-(trifluoromethyl)phenyl)-3-methyl-1-(tetrahydro-2H-pyran-4-yl)pyrazolo[1,5-c]quinazolin-2(3H)-one (Example 10);

9-(4-(4-(ethylamino)piperidin-1-yl)-3-(trifluoromethyl)phenyl)-3-methyl-1-(tetrahydro-2H-pyran-4-yl)pyrazolo[1,5-c]quinazolin-2(3H)-one (Example 11);

9-(6-(3-(dimethylamino)propoxy)pyridin-3-yl)-3-methyl-1-morpholinopyrazolo[1,5-c]quinazolin-2(3H)-one (Example 12);

9-(6-(3-(dimethylamino)propoxy)pyridin-3-yl)-1-((2S,6R)-2,6-dimethylmorpholino)-3-methylpyrazolo[1,5-c]quinazolin-2(3H)-one (Example 13);

9-(6-(3-(dimethylamino)propoxy)pyridin-3-yl)-3-methyl-1-(piperidin-1-yl)pyrazolo[1,5-c]quinazolin-2(3H)-one (Example 14);

9-(6-(3-(dimethylamino)propoxy)pyridin-3-yl)-3-methyl-1-(4-methylpiperazin-1-yl)pyrazolo[1,5-c]quinazolin-2(3H)-one (Example 15);

9-(6-(3-(dimethylamino)propoxy)pyridin-3-yl)-1-((3S,5R)-3,5-dimethylpiperazin-1-yl)-3-methylpyrazolo[1,5-c]quinazolin-2(3H)-one (Example 16);

9-(6-(3-(dimethylamino)propoxy)pyridin-3-yl)-3-methyl-1-((3S,5R)-3,4,5-trimethylpiperazin-1-yl)pyrazolo[1,5-c]quinazolin-2(3H)-one (Example 17);

9-(6-(3-(dimethylamino)propoxy)pyridin-3-yl)-1-((3S,5R)-4-ethyl-3,5-dimethylpiperazin-1-yl)-3-methylpyrazolo[1,5-c]quinazolin-2(3H)-one (Example 18);

9-(6-(3-(dimethylamino)propoxy)pyridin-3-yl)-1-isopropyl-3-methylpyrazolo[1,5-c]quinazolin-2(3H)-one (Example 19);

9-(6-(3-(piperidin-1-yl)propoxy)pyridin-3-yl)-1-isopropyl-3-methyl-pyrazolo[1,5-c]quinazolin-2(3H)-one (Example 20);

9-(4-(4-(dimethylamino)piperidin-1-yl)-3-fluorophenyl)-1-isopropyl-3-methylpyrazolo[1,5-c]quinazolin-2(3H)-one (Example 21);

9-(3-chloro-4-(4-(dimethylamino)piperidin-1-yl)phenyl)-1-isopropyl-3-methylpyrazolo[1,5-c]quinazolin-2(3H)-one (Example 22);

9-(4-(4-(dimethylamino)piperidin-1-yl)-3-(trifluoromethyl)phenyl)-1-isopropyl-3-methylpyrazolo[1,5-c]quinazolin-2(3H)-one (Example 23);

9-(4-(3-(dimethylamino)propoxy)-3-fluorophenyl)-1-isopropyl-3-methylpyrazolo[1,5-c]quinazolin-2(3H)-one (Example 24);

9-(4-(3-(dimethylamino)propoxy)-3-(trifluoromethyl)phenyl)-1-isopropyl-3-methylpyrazolo[1,5-c]quinazolin-2(3H)-one (Example 25);

9-(6-(3-(dimethylamino)propoxy)pyridin-3-yl)-3-ethyl-1-(tetrahydro-2H-pyran-4-yl)pyrazolo[1,5-c]quinazolin-2(3H)-one (Example 26);

9-(6-(4-(dimethylamino)piperidin-1-yl)pyridin-3-yl)-1-((2S,6R)-2,6-dimethylmorpholino)-3-methylpyrazolo[1,5-c]quinazolin-2(3H)-one (Example 27);

9-(3-fluoro-4-(3-(piperidin-1-yl)propoxy)phenyl)-1-isopropyl-3-methylpyrazolo[1,5-c]quinazolin-2(3H)-one (Example 28);

or stereoisomers, tautomers, N-oxides, hydrates, isotope-substituted derivatives, solvates or pharmaceutically acceptable salts thereof, or mixtures thereof, or prodrugs.

The term "hydrogen (H)" as employed herein includes its isotopes D and T.

The term "alkyl" as employed herein refers to alkyl itself or straight or branched chain radicals of up to ten carbons. Useful alkyl groups include straight-chained or branched $C_{1-10}$ alkyl groups, more preferably $C_{1-6}$ alkyl groups, e.g., $C_{1-4}$ alkyl. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein means a straight or branched chain radical of 2-10 carbon atoms, unless the chain length is limited thereto, wherein there is at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Useful alkoxy groups include oxygen substituted by $C_{1-10}$ alkyl groups, preferred $C_1$-$C_6$ alkoxy or $C_1$-$C_4$ alkoxy, mentioned above. The alkyl in the alkoxy group may be optionally substituted. Alkoxy substituents include, without limitation, halo, morpholino, amino including alkylamino and dialkylamino, and carboxy including esters thereof.

Useful alkylthio groups include sulfur substituted by $C_{1-10}$ alkyl groups. The alkyl in the alkylthio group may be optionally substituted. Also included are the sulfoxides and sulfones of such alkylthio groups.

Useful amino and optionally substituted amino groups include —$NR_{11}R_{12}$, wherein $R_{11}$ and $R_{12}$ are hydrogen, optionally substituted $C_{1-10}$ alkyl (e.g. $C_{1-6}$ alkyl or $C_{1-4}$ alkyl), optionally substituted cycloalkyl, aryl, optionally substituted heteroaryl or amino; or $R_{11}$ and $R_{12}$ are combined with the N to form a 4-8 membered heterocyclic ring structure, preferably a 5-8 membered heterocyclic group (e.g. piperidyl); or $R_6$ and $R_7$ are combined with the N and an additional N or O atom to form a 5-8 membered heterocyclic ring, such as piperazinyl. The alkyl and heterocyclic ring are optionally substituted.

Useful halo or halogen groups include fluoro, chloro, bromo and iodo.

The term "aryl" as employed herein by itself or as part of another group refers to monocyclic, bicyclic or tricyclic aromatic groups containing from 6 to 14 carbon atoms in the ring portion.

Useful aryl groups include $C_6$-$C_{14}$ aryl, preferably $C_6$-$C_{10}$ aryl. Typical $C_6$-$C_{14}$ aryl groups include phenyl, naphthyl, phenanthrenyl, anthracenyl, indenyl, azulenyl, biphenyl, biphenylenyl and fluorenyl groups.

The term "heteroaryl" as employed herein refers to groups having 5 to 14 ring atoms; 6, 10 or 14 π electrons shared in a cyclic array; and containing, as ring atom, carbon atoms and 1-3 heteroatoms selected from oxygen, nitrogen and sulfur.

Useful heteroaryl groups include thienyl (thiophenyl), benzo[d]isothiazol-3-yl, benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, imidazolyl, pyrazolyl, pyridyl (pyridinyl, including without limitation 2-pyridyl, 3-pyridyl, and 4-pyridyl), pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-amino-isocoumarin, pyrido[1,2-a]pyrimidin-4-one, tetrahydrocyclopenta[c]pyrazol-3-yl, pyrazolo[1,5-a]pyrimidinyl, pyrrolopyridyl such as pyrrolo[2,3-b]pyridyl, benzoisoxazolyl such as 1,2-benzoisoxazol-3-yl, benzimidazolyl, 2-oxindolyl, thiadiazolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "carbocycle (carbocyclic group)" as employed herein include cycloalkyl and partially saturated carbocyclic groups. Useful cycloalkyl groups are $C_3$-$C_8$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

The term "heterocycle (heterocyclic group)" is used herein to mean a saturated or partially saturated 3-8 membered monocyclic, or 7-10 membered bicyclic ring system, which consists of carbon atoms and one to four heteroatoms independently selected from the group consisting of O, N, and S, wherein the nitrogen and sulfur heteroatoms can be optionally oxidized, the nitrogen can be optionally quaternized. The term also includes any bicyclic group in which any of the above-defined heterocyclic rings is fused to a benzene ring. The heterocyclic ring of heterocycle can be substituted on carbon or on a nitrogen atom if the resulting compound is stable.

Useful saturated or partially saturated heterocyclic groups include tetrahydrofuranyl, tetrahydropyranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups, which are optionally substituted.

In this disclosure, when substituted, the aryl, heteroaryl, carbocyclic and heterocyclic groups may be substituted by one or more (such as 1, 2, 3, or 4) substituents selected from the group consisting of halo, hydroxy, carboxyl, amino, nitro, cyano, $C_{1-6}$ acylamino, $C_{1-6}$ acyloxy, $C_{1-6}$ alkoxy, aryloxy, alkylthio, $C_{1-6}$ alkyl, $C_{6-10}$ aryl, $C_{3-8}$ cycloalkyl, $C_{2-6}$ alkenyl, $C_{2-6}$ alkynyl, $C_{6-10}$ aryl($C_{2-6}$)alkenyl, $C_{6-10}$ aryl($C_{2-6}$)alkynyl, saturated and unsaturated heterocyclic and heteroaryl, methylenedioxy, $C_{1-6}$ haloalkyl, $C_{6-10}$ aryl ($C_{1-6}$)alkyl, $C_{1-6}$ hydroxyalkyl, ureido, thiol, azido, carbonyl, di($C_{1-10}$ alkyl)amino, alkylsulfonyl, aminosulfonyl, dialkylaminosulfonyl, and alkylsulfiniyl, and the like. The substituent itself may also be optionally substituted.

In this disclosure, when substituted, alkyl, alkoxy, alkylthio, alkenyl, alkynyl, and cycloalkyl may be optionally substituted by one or more (such as 1, 2, 3, or 4) substituents selected from the group consisting of halo, hydroxy, carboxyl, amino, nitro, cyano, $C_{1-6}$ acylamino, $C_{1-6}$ acyloxy, $C_{1-6}$ alkoxy, aryloxy, alkylthio, $C_{1-6}$ alkyl, $C_{6-10}$ aryl, $C_{3-8}$ cycloalkyl, $C_{2-6}$ alkenyl, $C_{2-6}$ alkynyl, $C_{6-10}$ aryl($C_{2-6}$)alkenyl, $C_{6-10}$ aryl($C_{2-6}$)alkynyl, saturated and unsaturated heterocyclic and heteroaryl, methylenedioxy, $C_{1-6}$ haloalkyl, $C_{6-10}$ aryl($C_{1-6}$)alkyl, $C_{1-6}$ hydroxyalkyl, ureido, thiol, azido, carbonyl, di($C_{1-10}$ alkyl)amino, alkylsulfonyl, aminosulfonyl, dialkylaminosulfonyl, and alkylsulfiniyl, and the like. The substituent itself may also be optionally substituted.

In preferred embodiments, when substituted, alkyl, alkoxy, alkylthio, alkenyl, alkynyl, cycloalkyl, carbonyl, carbocyclic and heterocyclic groups, may be optionally substituted by one or more (such as 1, 2, 3, or 4) substituents selected from the group consisting of halo, hydroxy, carboxyl, amino, nitro, cyano, $C_{1-6}$ acylamino, $C_{1-6}$ acyloxy, $C_{1-6}$ alkoxy, aryloxy, alkylthio, $C_{1-6}$ alkyl, $C_{6-10}$ aryl, $C_{3-8}$ cycloalkyl, $C_{2-6}$ alkenyl, $C_{2-6}$ alkynyl, $C_{6-10}$ aryl($C_{2-6}$)alkenyl, $C_{6-10}$ aryl($C_{2-6}$)alkynyl, saturated and unsaturated heterocyclic and heteroaryl.

It should be understood that in each embodiment, when the substituent is an aryl or a substituent with an aryl, a heterayl, or a substituent with a heterayl, or a heterocyclic group or a substituent with a heterocyclic group, the number thereof is usually 1.

The term "arylalkyl" is used herein to mean any of the above-mentioned $C_{1-10}$ alkyl groups substituted by any of the above-mentioned $C_{6-14}$ aryl groups. Preferably the arylalkyl group is benzyl, phenethyl or naphthylmethyl.

The term "arylalkenyl" is used herein to mean any of the above-mentioned $C_{2-10}$ alkenyl groups substituted by any of the above-mentioned $C_{6-14}$ aryl groups.

The term "arylalkynyl" is used herein to mean any of the above-mentioned $C_{2-10}$ alkynyl groups substituted by any of the above-mentioned $C_{6-14}$ aryl groups.

The term "aryloxy" is used herein to mean oxygen substituted by any of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{1-10}$ alkoxy groups substituted by any of the above-mentioned aryl groups, which may be optionally substituted. Useful arylalkoxy groups include benzyloxy and phenethyloxy.

Useful haloalkyl groups include $C_{1-10}$ alkyl, or preferably $C_{1-6}$ alkyl substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido. Useful acyl includes $C_{1-6}$ acyl, such as acetyl. The acyl group may be optionally substituted, for example, it may be optionally substituted with one or several (within 6) substituents selected from aryl and halogen, wherein, the aryl group may be optionally substituted. For example, the substituted amido groups include chloroacetamido and pentafluorobenzamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy. Similarly, the acyl group of the acyloxy group may be optionally substituted, for example, it may be optionally substituted with one or more (within 6) substituents selected from aryl and halogen.

Some of the compounds of the present disclosure may exist as stereoisomers including optical isomers. The disclosure includes all stereoisomers and both the racemic mixtures of such stereoisomers as well as the individual enantiomers that may be separated according to methods that are well known to those of ordinary skill in the art.

Examples of pharmaceutically acceptable salts include inorganic and organic acid salts, such as hydrochloride, hydrobromide, phosphate, sulphate, citrate, lactate, tartrate, maleate, fumarate, mandelate and oxalate; and inorganic and organic base salts with bases, such as sodium hydroxy, tris(hydroxymethyl)aminomethane (TRIS, tromethamine) and N-methyl-glucamine.

Examples of prodrugs of the compounds of the disclosure include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The present disclosure also includes all appropriate isotopic variations of the compound of the present disclosure or a pharmaceutically acceptable salt thereof. The isotopic change of the compound of the present disclosure or a pharmaceutically acceptable salt thereof means that at least one atom is replaced by an atom having the same atomic number but having an atomic mass different from the atomic mass normally found in nature. Isotopes that can be introduced into the compounds of the present disclosure or their pharmaceutically acceptable salts include, but are not limited to H, C, N and O, such as $^{2}H$, $^{3}H$, $^{11}C$, $^{13}C$, $^{14}C$, $^{15}N$, $^{17}O$, $^{18}O$, $^{35}S$, $^{18}F$, $^{36}Cl$ and $^{125}I$. The appropriate isotopic derivative of the compound of the present disclosure or its pharmaceutically acceptable salt can be prepared by conventional techniques using appropriate isotopic derivatives of appropriate reagents.

The compounds of this disclosure may be prepared by using methods known to those skilled in the art, or the novel methods of this disclosure. Specifically, the compounds of this disclosure with Formula I, IIa, IIb or III can be prepared as illustrated by the exemplary reaction in Scheme 1. Heating reaction of 2-(tetrahydro-2H-pyran-4-yl)acetic acid and concentrated sulfuric acid in methanol produced methyl 2-(tetrahydro-2H-pyran-4-yl)acetate. Reaction of methyl 2-(tetrahydro-2H-pyran-4-yl)acetate and lithium diisopropylamide in anhydrous tetrahydrofuran at low temperature, followed by the addition of a solution of 5-bromo-2-nitrobenzaldehyde in anhydrous tetrahydrofuran, and the reaction of the mixture at room temperature produced methyl 3-(5-bromo-2-nitrophenyl)-3-hydroxy-2-(tetrahydro-2H-pyran-4-yl)propanoate. Heating reaction of methyl 3-(5-bromo-2-nitrophenyl)-3-hydroxy-2-(tetrahydro-2H-pyran-4-yl)propanoate and pyridinium dichromate in DCM produced methyl 3-(5-bromo-2-nitrophenyl)-3-oxo-2-(tetrahydro-2H-pyran-4-yl)propanoate. Heating reaction of methyl 3-(5-bromo-2-nitrophenyl)-3-oxo-2-(tetrahydro-2H-pyran-4-yl)propanoate and hydrazinium hydroxide solution produced 5-(5-bromo-2-nitrophenyl)-4-(tetrahydro-2H-pyran-4-yl)-1,2-dihydro-3H-pyrazol-3-one. Heating reaction of 5-(5-bromo-2-nitrophenyl)-4-(tetrahydro-2H-pyran-4-yl)-1,2-dihydro-3H-pyrazol-3-one and stannous chloride dihydride in ethanol produced 5-(2-amino-5-bromophenyl)-4-(tetrahydro-2H-pyran-4-yl)-1,2-dihydro-3H-pyrazol-3- one. Heating reaction of 5-(2-amino-5-bromophenyl)-4-(tetrahydro-2H-pyran-4-yl)-1,2-dihydro-3H-pyrazol-3-one, trimethoxymethane and toluenesulfonic acid in tetrahydrofuran produced 9-bromo-1-(tetrahydro-2H-pyran-4-yl)pyrazolo[1,5-c]quinazolin-2(3H)-one. Heating reaction of 9-bromo-1-(tetrahydro-2H-pyran-4-yl)pyrazolo[1,5-c]quinazolin-2(3H)-one, (6-(3-(dimethylamino)propyl)pyridin-3-yl)boronic acid pinacol ester, cesium carbonate and [1,1'-Bis(diphenylphosphino)ferrocene]dichloropalladium(II) in dioxane and water produced 9-(6-(3-(dimethylamino)propoxy)pyridin-3-yl)-1-(tetrahydro-2H-pyran-4-yl)pyrazolo[1,5-c]quinazolin-2(3H)-one.

Scheme 1

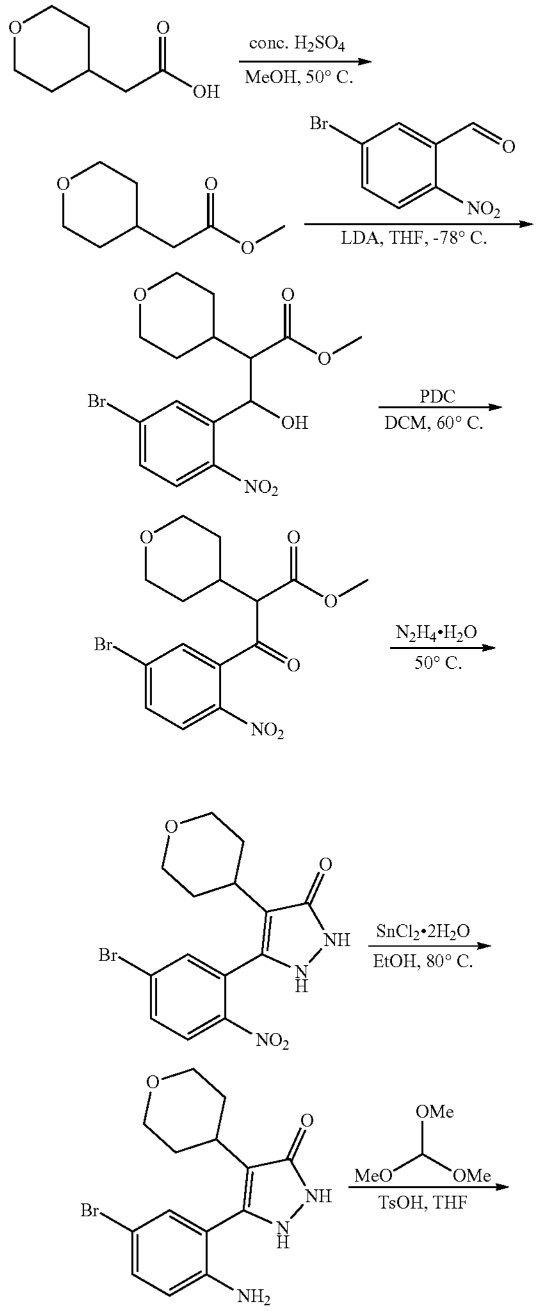

-continued

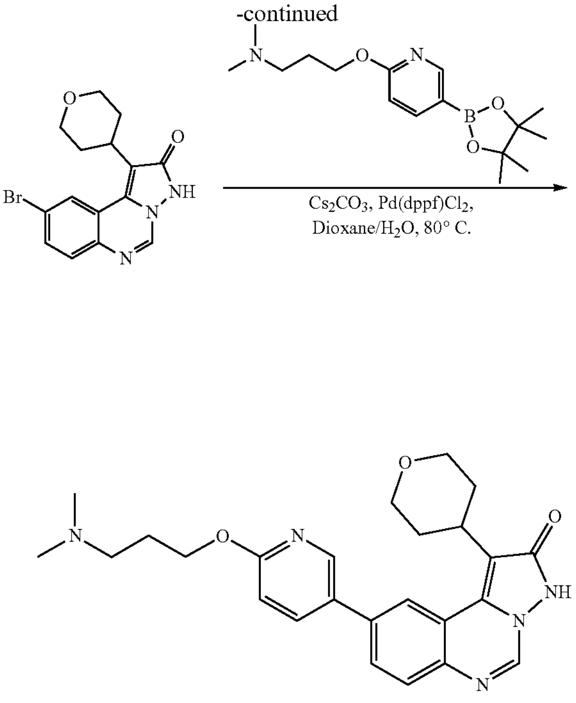

The compounds of this disclosure can be prepared as illustrated by the exemplary reaction in Scheme 2. Reaction of 5-(5-bromo-2-nitrophenyl)-4-(tetrahydro-2H-pyran-4-yl)-1,2-dihydro-3H-pyrazol-3-one, DIPEA and a DCM solution of di-tert-butyl dicarbonate in methanol at room temperature produced tert-butyl 5-(5-bromo-2-nitrophenyl)-3-oxo-4-(tetrahydro-2H-pyran-4-yl)-2,3-dihydro-1H-pyrazole-1-carboxylate. Heating reaction of tert-butyl 5-(5-bromo-2-nitrophenyl)-3-oxo-4-(tetrahydro-2H-pyran-4-yl)-2,3-dihydro-1H-pyrazole-1-carboxylate and iodomethane in DMF produced tert-butyl 5-(5-bromo-2-nitrophenyl)-2-methyl-3-oxo-4-(tetrahydro-2H-pyran-4-yl)-2,3-dihydro-1H-pyrazole-1-carboxylate. Reaction of tert-butyl 5-(5-bromo-2-nitrophenyl)-2-methyl-3-oxo-4-(tetrahydro-2H-pyran-4-yl)-2,3-dihydro-1H-pyrazole-1-carboxylate and HCl in dioxane at room temperature produced 5-(5-bromo-2-nitrophenyl)-2-methyl-4-(tetrahydro-2H-pyran-4-yl)-1,2-dihydro-3H-pyrazol-3-one hydrochloride. Reaction of 5-(5-bromo-2-nitrophenyl)-2-methyl-4-(tetrahydro-2H-pyran-4-yl)-1,2-dihydro-3H-pyrazol-3-one hydrochloride, Zn and $NH_4Cl$ in the mixture solution of methanol and water at room temperature produced 5-(2-amino-5-bromophenyl)-2-methyl-4-(tetrahydro-2H-pyran-4-yl)-1,2-dihydro-3H-pyrazol-3-one. Heating reaction of 5-(2-amino-5-bromophenyl)-2-methyl-4-(tetrahydro-2H-pyran-4-yl)-1,2-dihydro-3H-pyrazol-3-one, TsOH·$H_2O$ and trimethoxymethane in THF produced 9-bromo-3-methyl-1-(tetrahydro-2H-pyran-4-yl)pyrazolo[1,5-c]quinazolin-2(3H)-one. Heating reaction of 9-bromo-3-methyl-1-(tetrahydro-2H-pyran-4-yl)pyrazolo[1,5-c]quinazolin-2(3H)-one, (6-(3-(dimethylamino)propyl)pyridin-3-yl)boronic acid pinacol ester, cesium carbonate and [1,1'-bis(diphenylphosphino)ferrocene]dichloropalladium in dioxane and water produced the target compound 9-(6-(3-(dimethylamino)propoxy)pyridin-3-yl)-3-methyl-1-(tetrahydro-2H-pyran-4-yl)pyrazolo[1,5-c]quinazolin-2(3H)-one.

Scheme 2

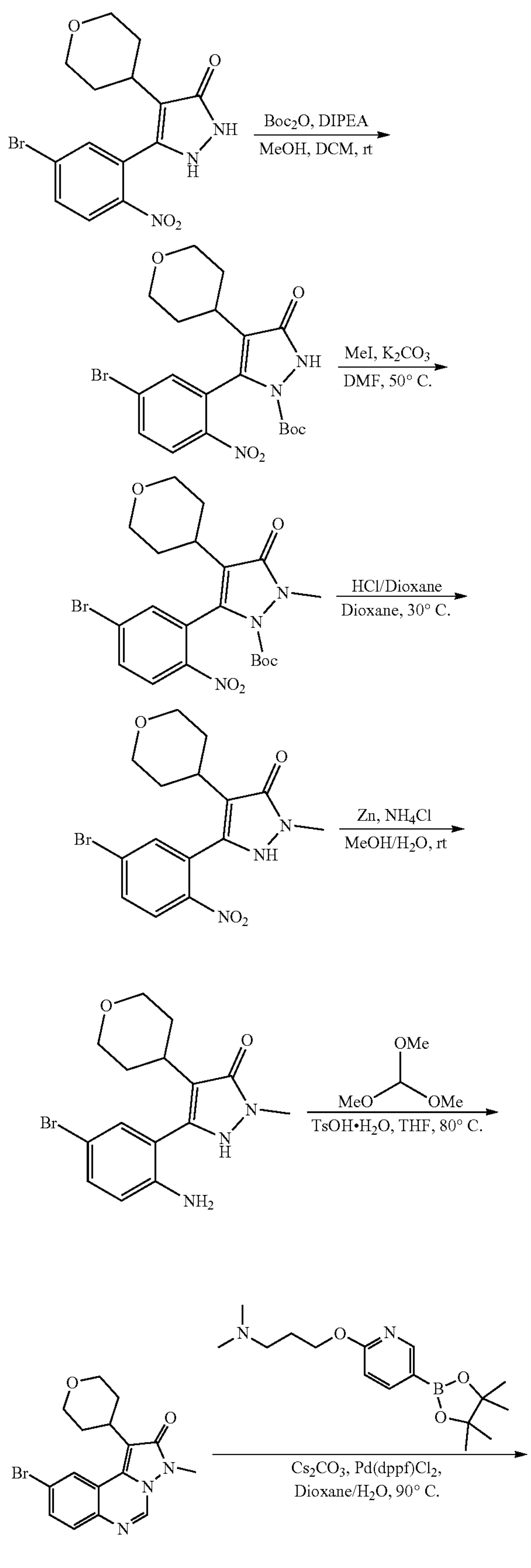

-continued

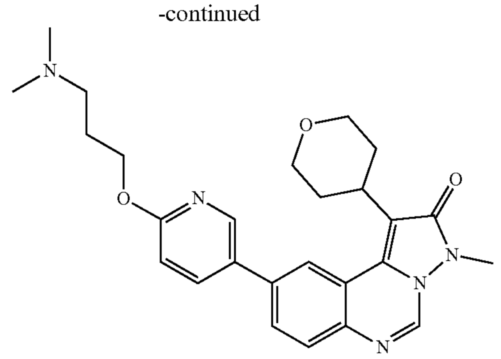

Other related compounds can be prepared using similar methods. For example, replacement of (6-(3-(dimethylamino)propyl)pyridin-3-yl)boronic acid pinacol ester with N,N-dimethyl-3-(4-(4,4,5,5-tetramethyl-1,3,2-dioxaborolan-2-yl)-2-(trifluoromethyl)phenoxy)propan-1-amine produced the targeted compound 9-(4-(3-(dimethylamino)propoxy)-3-(trifluoromethyl)phenyl)-3-methyl-1-(tetrahydro-2H-pyran-4-yl)pyrazolo[1,5-c]quinazolin-2(3H)-one. Replacement of (6-(3-(dimethylamino)propyl)pyridin-3-yl)boronic acid pinacol ester with 1-(2-fluoro-4-(4,4,5,5-tetramethyl-1,3,2-dioxaborolan-2-yl)phenyl)-N,N-dimethylpiperidin-4-amine produced the targeted compound 9-(4-(4-(dimethylamino)piperidin-1-yl)-3-fluorophenyl)-3-methyl-1-(tetrahydro-2H-pyran-4-yl)pyrazolo[1,5-c]quinazolin-2(3H)-one. Replacement of 5-(5-bromo-2-nitrophenyl)-2-methyl-4-(tetrahydro-2H-pyran-4-yl)-1,2-dihydro-3H-pyrazol-3-one with 5-(5-bromo-2-nitrophenyl)-4-isopropyl-2-methyl-1,2-dihydro-3H-pyrazol-3-one produced the targeted compound 9-(6-(3-(dimethylamino)propoxy)pyridin-3-yl)-1-isopropyl-3-methylpyrazolo[1,5-c]quinazolin-2(3H)-one. Replacement of (6-(3-(dimethylamino)propyl)pyridin-3-yl)boronic acid pinacol ester with 2-(3-(piperidin-1-yl)propoxy)-5-(4,4,5,5-tetramethyl-1,3,2-dioxaborolan-2-yl)pyridine produced the targeted compound 9-(6-(3-(piperidin-1-yl)propoxy)pyridine-3-yl)-1-isopropyl-3-methylpyrazolo[1,5-c]quinazolin-2(3H)-one. Replacement of (6-(3-(dimethylamino)propyl)pyridin-3-yl)boronic acid pinacol ester with N,N-dimethyl-1-(4-(4,4,5,5-tetramethyl-1,3,2-dioxaborolan-2-yl)-2-(trifluoromethyl)phenyl)piperidin-4-amine produced the targeted compound 9-(4-(4-(dimethylamino)piperidin-1-yl)-3-(trifluoromethyl)phenyl)-1-isopropyl-3-methylpyrazolo[1,5-c]quinazolin-2(3H)-one. Replacement of iodomethane with iodoethane produced the targeted compound 9-(6-(3-(dimethylamino)propoxy)pyridin-3-yl)-3-ethyl-1-(tetrahydro-2H-pyran-4-yl)pyrazolo[1,5-c]quinazolin-2(3H)-one.

One important aspect of the present disclosure is the find that the compounds of Formulae I, IIa, IIb and III are kinase inhibitors, especially ATM kinase inhibitors. Therefore, these compounds can be used to treat or prevent a variety of clinical diseases caused by DDR dysfunction or diseases that benefit from the inhibition of kinase activity. Therefore, the present invention provides the use of compounds of Formulae I, IIa, IIb and III in the preparation of drugs for the treatment or prevention of clinical conditions caused by DDR functional defects or diseases that benefit from the inhibition of kinase activity.

The present disclosure also includes a method for the treatment or prevention of a DDR-mediated disease or a kinase-mediated disease, the method comprising administering to a subject an effective amount of a compound of Formula I, IIa, IIb or III, or its stereoisomers, tautomers, N-oxides, hydrates, isotopically substituted derivatives, solvates or pharmaceutically acceptable salts thereof, or mixtures thereof, or prodrugs thereof, or a pharmaceutical composition comprising an effective amount of Formula I, IIa, IIb or III, or its stereoisomers, tautomers, N-oxides, hydrates, isotopically substituted derivatives, solvates or pharmaceutically acceptable salts thereof, or mixtures thereof, or prodrugs thereof.

In the present disclosure, the treatment or prevention method is used for the treatment or prevention of clinical conditions caused by DDR dysfunction or diseases benefiting from the inhibition of kinase activity, or DDR-mediated or kinase-mediated diseases, such as cancer. Such diseases include, but are not limited to, liver cancer, melanoma, Hodgkin's disease, non-Hodgkin's lymphoma, acute lymphoid leukemia, chronic lymphoid leukemia, multiple myeloma, neuroblastoma, breast cancer, ovarian cancer, lung cancer, Wilms tumor, cervical cancer, testicular cancer, soft tissue sarcoma, primary macroglobulinemia, bladder cancer, chronic myeloid leukemia, primary brain cancer, malignant melanoma, small cell lung cancer, gastric cancer, colon cancer, malignant pancreatic islet tumor, malignant carcinoid cancer, choriocarcinoma, granuloma fungoides, head and neck cancer, osteogenic sarcoma, pancreatic cancer, acute myeloid leukemia, hairy cell leukemia, rhabdomyosarcoma, Kaposi's sarcoma, urogenital tumor disease, thyroid cancer, esophageal cancer, malignant hypercalcemia, cervical hyperplasia, renal cell carcinoma, endometrial cancer, polycythemia vera, idiopathic thrombocytosis, adrenal cortical cancer, skin cancer, prostate cancer, and Huntington's disease. In the present disclosure, the kinase includes ATM (ataxia-telangiectasia mutant gene) kinase; therefore, in some embodiments, the cancer described in the present invention is an ATM kinase-mediated cancer, which preferably benefits from the inhibition of ATM kinase activity.

In practicing the therapeutic methods, effective amounts of compositions containing therapeutically effective concentrations of the compounds of Formula I, IIa, IIb or III, or its stereoisomers, tautomers, N-oxides, hydrates, isotopically substituted derivatives, solvates or pharmaceutically acceptable salts thereof, or mixture, or prodrug, which is formulated for oral, intravenous, local or topical application, for the treatment of cancer and other diseases, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to an effective regimen. The amount may cure the disease but, typically, is administered in order to ameliorate the symptoms of the disease. Typically, repeated administration is required to achieve the desired amelioration of symptom.

In another embodiment, there is provided a pharmaceutical composition comprising a kinase inhibitor of Formula I or a pharmaceutically acceptable salt thereof and a pharmaceutically acceptable carrier.

Another embodiment of the present disclosure is directed to a pharmaceutical composition effective to treat or prevent cancer comprising a compound of Formula I, IIa, IIb or III, or its stereoisomers, tautomers, N-oxides, hydrates, isotopically substituted derivatives, solvates or pharmaceutically acceptable salts thereof, or mixture, or prodrug, which functions as a kinase inhibitor, in combination with at least one known anticancer agent or a pharmaceutically acceptable salt thereof. In particular, the compound herein can be combined with other anticancer drugs related to the mechanism of DNA damage and repair, including PARP inhibitors Olaparib, Niraprib, Rucaparib, Talazoparib and Senaparib; HDAC inhibitors Vorinostat, Romidepsin, Panobinostat and Belinostat; and so on. And the compound herein can be combined with other anticancer drugs related to cell division detection sites, including Chk1/2 inhibitors, CDK4/6 inhibitors such as Palbociclib, ATR inhibitors, Weel inhibitors, DNA-PK inhibitors, and so on. Other known anti-cancer drugs that can be used in anti-cancer combination therapy include but are not limited to alkylating agents such as busulfan, melphalan, chlorambucil, cyclophosphamide, ifosfamide, temozolomide, bendamustine, cisplatin, mitomycin C, bleomycin and carboplatin; topoisomerase I inhibitors such as camptothecin, irinotecan and topotecan; topoisomerase II inhibitors such as doxorubicin, Epirubicin, Aclarithromycin, Mitoxantrone, Methylhydroxyellipticine and Mintopopol; RNA/DNA antimetabolites such as 5-azacytidine, gemcitabine, 5-fluorouracil, capecita And methotrexate; DNA anti-metabolites such as 5-fluoro-2'-deoxyuridine, fludarabine, nelarabine, cytarabine, pratroxa, pemetrexed, hydroxyurea and thioguanine; antimitotic agents such as colchicine, vinblastine, vincristine, vinorelbine, paclitaxel, ixabepilone, cabazitaxel and docetaxel; antibodies such as monoclonal antibodies, panitumumab, Nezotuzumab, nivolumab, pembrolizumab, ramucirumumab, bevacizumab, pertuzumab, trastuzumab, cetuximab, obin Eutastuzumab, Ofatumumab, Rituximab, Alemtuzumab, Titumomab, Tositumomab, Bentuximab, Daratumumab, Errotuzumab Lizumab, T-DM1, Ofatumumab, Dinutuximab, Blinatumomab, Ipilimumab, Avastin, Herceptin, and Rituxan; kinase inhibitors such as imatinib, gefitinib, erlotinib, and Steinib, Afatinib, Ceritinib, Alectinib, Crizotinib, Erlotinib, Lapatinib, Sorafenib, Reggafenib, Verofenib, Dala Fenib, aflibercept, sunitinib, nilotinib, dasatinib, bosutinib, pratinib, ibrutinib, cabotinib, levatinib, van der Tanib, trametinib, carbitinib, axitinib, temsirolimus, Idelalisib, pazopanib, tecarinib, and everolimus. Other known anti-cancer drugs that can be used for anti-cancer combination therapy include tamoxifen, letrozole, fulvestrant, mitogen hydrazone, octreotide, retinoic acid, arsenic, zoledronic acid, bortezomib, Carfilzomib, Ixazomib, Vimodji, Sondeji, Denosumab, Thalidomide, Lenalidomide, Venetoclax, Aldesleukin (Recombinant Human Interleukin-2) and Sipueucel-T (Prostate Cancer Vaccine)).

In practicing the methods of the present disclosure, the compound of the disclosure may be administered together with at least one known anticancer agent as part of a unitary pharmaceutical composition. Alternatively, the compound of the disclosure may be administered apart from at least one known anticancer agent. In one embodiment, the compound of the disclosure and at least one known anticancer agent are administered substantially simultaneously, i.e. the compounds are administered at the same time or one after the other, so long as the compounds reach therapeutic levels in the blood at the same time. In another embodiment, the compound of the disclosure and at least one known anticancer agent are administered according to their individual dose schedule, so long as the compounds reach therapeutic levels in the blood.

Another embodiment of the present disclosure is directed to a bioconjugate, which functions as a kinase inhibitor, that comprises a compound described herein and is effective to inhibit neoplasia. The bioconjugate that inhibits neoplasia is consisted of a compound described herein and at least one known therapeutically useful antibody, such as trastuzumab or rituximab, growth factors, such as EGF, FGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of the therapeutically useful antibodies, such as trastuzumab or rituximab.

Similarly, another embodiment of the present disclosure is directed to a composition effective to inhibit neoplasia comprising a compound of Formula I, IIa, IIb or III, or its stereoisomers, tautomers, N-oxides, hydrates, isotopically substituted derivatives, solvates or pharmaceutically acceptable salts thereof, or mixture, or prodrug, which functions as a kinase inhibitor, in combination with radiation therapy. In this embodiment, the compound of the disclosure may be administered at the same time as the radiation therapy is administered or at a different time.

Yet another embodiment of the present disclosure is directed to a composition effective for post-surgical treatment of cancer, comprising a compound of Formula I, IIa, IIb or III, or its stereoisomers, tautomers, N-oxides, hydrates, isotopically substituted derivatives, solvates or pharmaceutically acceptable salts thereof, or mixture, or prodrug, which functions as a kinase inhibitor. The disclosure also relates to a method of treating cancer by surgically removing the tumor and then treating the mammal with one of the pharmaceutical compositions described herein.

Pharmaceutical compositions within the scope of this disclosure include all compositions wherein the compounds of the present disclosure are contained in an amount that is effective to achieve its intended purpose. While individual needs vary, determination of optimal ranges of effective amounts of each component is within the skill of the art. Typically, the compounds or the pharmaceutically acceptable salt thereof may be administered to mammals, orally at a dose of from about 0.0025 to 50 mg/kg of body weight, per day. Preferably, from approximately 0.01 to approximately 10 mg/kg of body weight is orally administered. If a known anticancer agent is also administered, it is administered in an amount that is effective to achieve its intended purpose. The optimal amounts of such known anticancer agents effective for cancer are well known to those skilled in the art.

The unit oral dose may comprise from approximately 0.01 to approximately 50 mg, preferably approximately 0.1 to approximately 10 mg of the compound of the disclosure. The unit dose may be administered one or more times daily, as one or more tablets, each containing from approximately 0.1 to approximately 50 mg, conveniently approximately 0.25 to 10 mg of the compound or its solvates.

In a topical formulation, the compound may be present at a concentration of approximately 0.01 to 100 mg per gram of carrier.

In addition to administering the compound as a raw chemical, the compounds of the disclosure may be administered as part of a suitable pharmaceutical preparation containing pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, as well as suitable solutions for administration by injection or orally, contain from approximately 0.01 to 99 percent, preferably from approximately 0.25 to 75 percent of active compound(s), together with the excipient.

Also included within the scope of the present disclosure are the non-toxic pharmaceutically acceptable salts of the compounds of the present disclosure. Acid addition salts are formed by mixing a solution of the compounds of the present disclosure with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Base addition salts are formed by mixing a solution of the compounds of the present disclosure with a solution of a pharmaceutically acceptable non-toxic base, such as sodium hydroxide, potassium hydroxide, choline hydroxide, sodium carbonate, tris(hydroxymethyl)aminomethane (TRIS), N-methyl-glucamine and the like.

The pharmaceutical compositions of the disclosure may be administered to any mammal, so long as they may experience the therapeutic effects of the compounds of the disclosure. Foremost among such mammals are humans and veterinary animals, although the disclosure is not intended to be so limited.

The pharmaceutical compositions of the present disclosure may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present disclosure are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, including, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, tale, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethyl-cellulose phthalate, are used. Dye stuffs or pigments may be added to the tablets or dragee coatings, e.g., for identification or in order to characterize combinations of active compound doses.

Other pharmaceutical preparations, which may be used orally, include push-fit capsules made of gelatin, as well as soft, sealed capsules made of gelatin and a plasticizer, such as glycerol or sorbitol. The push-fit capsules may contain the active compounds in the form of granules, which may be mixed with fillers, such as lactose; binders, such as starches; and/or lubricants, such as talc or magnesium stearate and stabilizers. In soft capsules, the active compounds are preferably dissolved or suspended in suitable liquids, such as fatty oils, or liquid paraffin. In addition, stabilizers may be added.

Suitable formulations for parenteral administration include aqueous solutions of the active compounds, e.g., aqueous solutions and alkaline solutions of water-soluble salts. In addition, suspensions of the active compounds as appropriate oily injection suspensions may/be administered. Suitable lipophilic solvents or vehicles include fatty oils, e.g., sesame oil, or synthetic fatty acid esters, e.g., ethyl oleate or triglycerides or polyethylene glycol-400, or cremophor, or cyclodextrins. Aqueous injection suspensions may contain substances which increase the viscosity of the suspension, e.g., sodium carboxymethyl cellulose, sorbitol, and/or dextran. Optionally, the suspension may also contain stabilizers.

In accordance with one aspect of the present disclosure, compounds of the disclosure are employed in topical and parenteral formulations and are used for the treatment of skin cancer.

The topical compositions of this disclosure are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting, color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The following examples are illustrative, but not limiting, of the method and compositions of the present disclosure. Other suitable modifications and adaptations of the variety of conditions and parameters normally encountered in clinical therapy and which are obvious to those skilled in the art are within the spirit and scope of the disclosure.

EXAMPLES

General Remarks

All reagents were of commercial quality. Solvents were dried and purified by standard methods. Mass spectrum analyses were recorded on a Platform II (Agilent 6110) quadrupole mass spectrometer fitted with an electrospray rinterface. $^1$H NMR spectra was recorded at 400 MHz, on a Brücker Ascend 400 apparatus. Chemical shifts were recorded as parts per million (ppm) downfield from TMS (0.00 ppm), and J coupling constants were reported in hertz (Hz). In addition to the intermediate synthesis described in detail in the examples, the synthesis of a portion of the intermediate is also given below, in addition to the methods mentioned below, other intermediate substituted aryl groups may also be synthesized by known methods by those skilled in the art.

Example 1

9-(6-(3-(dimethylamino)propoxy)pyridin-3-yl)-1-(tetrahydro-2H-pyran-4-yl)pyrazolo[1,5-c]quinazolin-2(3H)-one

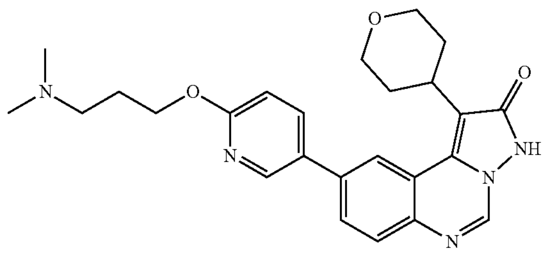 [SMILES: CN(C)CCCOc1ccc(-c2ccc3ncn4[nH]c(=O)c(C5CCOCC5)c4c3c2)cn1]

a) Preparation of methyl 2-(tetrahydro-2H-pyran-4-yl) acetate: 2-(tetrahydro-2H-pyran-4-yl)acetic acid (800 mg, 5.35 mmol) was dissolved in MeOH (10 mL), and concentrated sulfuric acid (0.5 mL) was added. The mixture was stirred at 50° C. overnight. The reaction solution was cooled to room temperature, the solvent was removed at reduced pressure. The residue was dissolved in EA (20 mL). The organic layers were washed with saturated sodium bicarbonate and brine, dried over anhydrous $Na_2SO_4$, filtered and concentrated under reduced pressure to give a crude product (900 mg, yellow oil).

b) Preparation of methyl 3-(5-bromo-2-nitrophenyl)-3-hydroxy-2-(tetrahydro-2H-pyran-4-yl)propanoate: methyl 2-(tetrahydro-2H-pyran-4-yl)acetate (2.3 g, 14.3 mmol) was dissolved in anhydrous THF (30 mL), LDA (9.8 mL, 19.56 mmol) was added dropwise at −78° C., then the mixture was stirred at −78° C. for 0.5 h. The 5-bromo-2-nitrobenzaldehyde (3.0 g, 13.04 mmol) in anhydrous THF solution was added dropwise to the mixture, then the mixture was slowly warmed up to room temperature and reacted for 2 hours. The reaction mixture was quenched with water and extracted with EA (100 mL×2). The combined organic layers were washed with brine, dried over anhydrous $Na_2SO_4$, filtered and concentrated under reduced pressure to give a crude product (5.3 g, yellow solid). LC-MS (ESI): $(M+H)^+/(M+2+H)^+$ 388.15/390.15.

c) Preparation of methyl 3-(5-bromo-2-nitrophenyl)-3-oxo-2-(tetrahydro-2H-pyran-4-yl)propanoate: methyl 3-(5-bromo-2-nitrophenyl)-3-hydroxy-2-(tetrahydro-2H-pyran-4-yl)propanoate (3.0 g, 7.73 mmol) and PDC (5.8 g, 15.46 mmol) was dissolved in DCM (100 mL), the mixture was stirred at 60° C. for 16 h. The reaction solution was cooled to room temperature, and the solvent was removed at reduced pressure. The residue was purified by column chromatography ($SiO_2$, EA:PE=1:1) to afford the target product (2.0 g, light yellow solid, 67% yield). LC-MS (ESI): m/z $(M+H)^+/(M+2+H)^+$ 386.05/388.05.

d) Preparation of 5-(5-bromo-2-nitrophenyl)-4-(tetrahydro-2H-pyran-4-yl)-1,2-dihydro-3H-pyrazol-3-one: methyl 3-(5-bromo-2-nitrophenyl)-3-oxo-2-(tetrahydro-2H-pyran-4-yl)propanoate (1.5 g, 3.88 mmol) was dissolved in hydrazinium hydroxide solution (5 mL), and the mixture was stirred at 50° C. for 4 h. The reaction mixture was diluted with EA (100 mL) and $H_2O$ (100 mL). The organic phase was separated, and the aqueous phase was extracted with EA (50 mL×2). The combined organic layers were washed with brine, dried over anhydrous $Na_2SO_4$, filtered and concentrated under reduced pressure to give a crude product (1.1 g, light yellow solid, 77% yield). LC-MS (ESI): m/z $(M+H)^+/(M+2+1)^+$ 368.10/370.10.

e) Preparation of 5-(2-amino-5-bromophenyl)-4-(tetrahydro-2H-pyran-4-yl)-1,2-dihydro-3H-pyrazol-3-one: 5-(5-bromo-2-nitrophenyl)-4-(tetrahydro-2H-pyran-4-yl)-1,2-dihydro-3H-pyrazol-3-one (1.1 g, 3.0 mmol) and stannous chloride dihydrate (1.4 g, 6.0 mmol) was dissolved in EtOH (30 mL), and the mixture was stirred at 80° C. for 2 h. The reaction solution was cooled to room temperature, and the mixture was purified by column chromatography ($SiO_2$, EA) to afford the target product (700 mg, yellow solid, 69% yield). LC-MS (ESI): m/z $(M+H)^+/(M+2+H)^+$ 338.10/340.10.

f) Preparation of 9-bromo-1-(tetrahydro-2H-pyran-4-yl)pyrazolo[1,5-c]quinazolin-2(3H)-one: 5-(2-amino-5-bromophenyl)-4-(tetrahydro-2H-pyran-4-yl)-1,2-dihydro-3H-pyrazol-3-one (650 mg, 1.92 mmol), trimethoxymethane (0.42 mL, 3.84 mmol) and p-toluenesulfonic acid (35 mg, 0.2 mmol) was dissolved in THF (20 mL), and the mixture was refluxed and stirred for 3 h. The mixture was purified by column chromatography ($SiO_2$, EA) to afford the target product (150 mg, yellow solid, 22% yield). LC-MS (ESI): m/z $(M+H)^+/(M+2+H)^+$ 348.10/350.10.

g) Preparation of 9-(6-(3-(dimethylamino)propoxy)pyridin-3-yl)-1-(tetrahydro-2H-pyran-4-yl)pyrazolo[1,5-c]quinazolin-2(3H)-one: 9-bromo-1-(tetrahydro-2H-pyran-4-yl)pyrazolo[1,5-c]quinazolin-2(3H)-one (120 mg, 0.34 mmol), (6-(3-(dimethylamino)propyl)pyridin-3-yl)boronic acid pinacol ester (126 mg, 0.41 mmol), $Cs_2CO_3$ (221 mg, 0.68 mmol) and Pd(dppf)$Cl_2$ (24 mg, 0.03 mmol) was dissolved in 1,4-dioxane (9 mL) and water (1 mL), and the mixture was stirred at 80° C. for 4 h under the protection of $N_2$. The reaction solution was cooled to room temperature, the reaction mixture was diluted with EA (50 mL) and $H_2O$ (50 mL), the organic phase was separated, and the aqueous phase was extracted with EA (50 mL×2). The combined organic layers were washed with brine, dried over anhydrous $Na_2SO_4$, filtered and concentrated under reduced pressure to give a crude product. The residue was purified by pre-HPLC (C18 column, 0-100% ACN/$H_2O$) to afford the target product (13 mg, white solid, 8% yield). LC-MS (ESI): m/z $(M+H^+)$ 448.31. $^1H$ NMR (400 MHz, DMSO-$d_6$): δ 8.96 (s, 1H), 8.61 (d, J=2.6 Hz, 1H), 8.33-8.29 (m, 2H), 8.14 (dd, J=8.6, 2.6 Hz, 1H), 7.95 (dd, J=8.5, 1.9 Hz, 1H), 7.88 (d, J=8.5 Hz, 1H), 6.98 (d, J=8.6 Hz, 1H), 4.36 (t, J=6.6 Hz, 2H), 4.00-3.96 (m, 2H), 3.58-3.50 (m, 4H), 2.39-2.35 (m, 2H), 2.23-2.19 (m, 1H), 2.16 (s, 6H), 1.91-1.86 (m, 2H), 1.73-1.68 (m, 2H).

Example 2

9-(6-(3-(dimethylamino)propoxy)pyridin-3-yl)-3-methyl-1-(tetrahydro-2H-pyran-4-yl)pyrazolo[1,5-c]quinazolin-2(3H)-one a) Preparation of tert-butyl 5-(5-bromo-2-nitrophenyl)-3-oxo-4-(tetrahydro-2H-pyran-4-yl)-2,3-dihydro-1H-pyrazole-1-carboxylate: To a mixture of 5-(5-bromo-2-nitrophenyl)-4-(tetrahydro-2H-pyran-4-yl)-1,2-dihydro-3H-pyrazol-3-one (6 g, 14.32 mmol) and DIPEA (3.70 g, 28.64 mmol, 4.99 mL) in MeOH (120 mL) was added $Boc_2O$ (4.69 g, 21.48 mmol, 4.94 mL) in DCM (120 mL) drop-wise at 10-15° C. over a period of 30 min. The mixture was stirred at 10-20° C. for 12 hours. The residue was concentrated in vacuum and purified by column chromatography ($SiO_2$, PE/EA=I/O to 0:1) to afford the target product (3.1 g, yellow gum, 42.71% yield). LC-MS (ESI): m/z $(M+H)^+/(M+2+H)^+$ 368.0/370.0.

b) Preparation of tert-butyl 5-(5-bromo-2-nitrophenyl)-2-methyl-3-oxo-4-(tetrahydro-2H-pyran-4-yl)-2,3-dihydro-1H-pyrazole-1-carboxylate: To a solution of tert-butyl 5-(5-bromo-2-nitrophenyl)-3-oxo-4-(tetrahydro-2H-pyran-4-yl)-2,3-dihydro-1H-pyrazole-1-carboxylate (3.0 g, 5.92 mmol) and $K_2CO_3$ (1.23 g, 8.88 mmol) in DMF (15 mL) was added iodomethane (1.68 g, 11.84 mmol, 737.00 μL) in one portion at 10° C. The reaction mixture was heated to 50° C. slowly and stirred at 50° C. for 12 hours. The residue was poured into water (50 mL) and extracted with ethyl acetate (100 mL×3). The combined organic phase was washed with brine (50 mL), dried with anhydrous $Na_2SO_4$, filtered and concentrated in vacuum. The residue was purified by column chromatography ($SiO_2$, PE:EA=1:1) to afford the target product (0.7 g, yellow solid, 21.73% yield). LC-MS (ESI): m/z $(M+H)^+/(M+2+H)^+$ 382.1/384.1 382.1. H NMR (400 MHz, $CDCl_3$): δ 8.10 (d, J=8.8 Hz, 1H), 7.82 (dd, J=8.8 Hz, 1H), 7.59 (d, J=2.4 Hz, 1H), 3.89 (d, J=11.6 Hz, 2H), 3.57 (s, 3H), 3.29-3.27 (m, 2H), 2.43-2.30 (m, 1H), 1.86-1.72 (m, 3H), 1.42-1.34 (m, 2H), 1.18-1.28 (m, 10H).

c) Preparation of 5-(5-bromo-2-nitrophenyl)-2-methyl-4-(tetrahydro-2H-pyran-4-yl)-1,2-dihydro-3H-pyrazol-3-one hydrochloride: To a solution of tert-butyl 5-(5-bromo-2-nitrophenyl)-2-methyl-3-oxo-4-(tetrahydro-2H-pyran-4-yl)-2,3-dihydro-1H-pyrazole-1-carboxylate (200 mg, 367.50 μmol) in dioxane (5 mL) was added HCl/dioxane (4 M, 5 mL) and the mixture was stirred at 30° C. for 12 h. The reaction mixture was concentrated under reduced pressure to give a crude product (150 mg, brown oil, 97.49% yield). LC-MS (ESI): m/z $(M+H)^+/(M+2+H)^+$ 382.0/384.0.

d) Preparation of 5-(2-amino-5-bromophenyl)-2-methyl-4-(tetrahydro-2H-pyran-4-yl)-1,2-dihydro-3H-pyrazol-3-one: To a solution of 5-(5-bromo-2-nitrophenyl)-2-methyl-4-(tetrahydro-2H-pyran-4-yl)-1,2-dihydro-3H-pyrazol-3-one hydrochloride (0.05 g, 119.43 μmol) in the mixture solution of MeOH (7 mL) and $H_2O$ (0.6 mL) was added $NH_4Cl$ (95.82 mg, 1.79 mmol) and Zn (62.47 mg, 955.41 μmol) at 25° C., and the mixture was stirred at 25° C. for 2 h. The reaction mixture was filtered and concentrated under reduced pressure to give a residue. The residue was dissolved in THF (10 mL) and the pH of the mixture was adjusted to 9 with $Et_3N$, and filtered, and then the organic layer was concentrated under reduced pressure to give a crude product (400 mg, brown solid, 97.49% yield). LC-MS (ESI): m/z $(M+H)^+/(M+2+H)^+$ 352.0/354.0.

e) Preparation of 9-bromo-3-methyl-1-(tetrahydro-2H-pyran-4-yl)pyrazolo[1,5-c]quinazolin-2(3H)-one: To a solution of 5-(2-amino-5-bromophenyl)-2-methyl-4-(tetrahydro-2H-pyran-4-yl)-1,2-dihydro-3H-pyrazol-3-one (0.04 g, 113.56 μmol) in THF (10 mL) was added TsOH·$H_2O$ (4.32 mg, 22.71 μmol) and trimethoxymethane (36.15 mg, 340.69 μmol, 37.35 μL). The mixture was stirred at 80° C. for 12 h. The reaction mixture was filtered and concentrated under reduced pressure to give a residue. The residue was purified by prep-TLC ($SiO_2$, DCM:MeOH=10:1) to afford the target product (33 mg, yellow solid, 80.22% yield). LC-MS (ESI): m/z $(M+H)^+/(M+2+H)^+$ 361.8/363.8.

f) Preparation of 9-(6-(3-(dimethylamino)propoxy)pyridin-3-yl)-3-methyl-1-(tetrahydro-2H-pyran-4-yl)pyrazolo[1,5-c]quinazolin-2(3H)-one: A mixture of 9-bromo-3-methyl-1-(tetrahydro-2H-pyran-4-yl)pyrazolo[1,5-c]quinazolin-2(3H)-one (23 mg, 63.50 μmol), (6-(3-(dimethylamino)propyl)pyridin-3-yl)boronic acid pinacol ester (27.35 mg, 89.32 μmol), $Cs_2CO_3$ (38.81 mg, 119.12 mol) an $Pd(dppf)Cl_2$ (8.72 mg, 11.92 μmol) in dioxane (10 mL) and $H_2O$ (0.5 mL) was degassed and purged with $N_2$ for 3 times, and then the mixture was stirred at 90° C. for 2 h under $N_2$ atmosphere. The reaction mixture was diluted with ACN (10 mL), filtered and concentrated under reduced pressure to give a residue. The residue was purified by prep-TLC ($SiO_2$, DCM:MeOH=5:1) to give a crude product, which was further purified by prep-HPLC (column:Waters Xbridge 150*25 mm*5 μm; mobile phase: [water (10 mM $NH_4HCO_3$)-ACN]; B %: 7%-37%, 10 min) to afford the target product (5 mg, yellow oil, 16.45% yield).

Examples 3-28 were prepared using the synthesis method similar to that described in Example 2, or they could be synthesized by a person skilled in the art according to known methods.

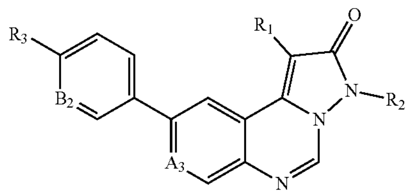

| Example | $R_3$ | $B_2$ | $A_3$ | $R_1$ | $R_2$ | MW/LC-MS (ESI) | $^1H$ NMR, 400 MHz |
|---|---|---|---|---|---|---|---|
| 2 | 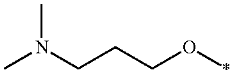 | N | CH | 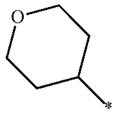 | $CH_3$ | $(M + H)^+$ 462.4 | $CD_3OD$: δ 8.77 (s, 1H), 8.50 (d, J = 2.4 Hz, 1H), 8.40 (d, J = 2 Hz, 1H), 8.07 (dd, J = 8.8 Hz, 1H), 7.98 (dd, J = 8.8 Hz, 1H), 7.86 (d, J = 8.8 Hz, 1H), 6.96 (dd, J = 8.8, 1H), 4.41 (t, J = 6.4 Hz, 2H), 4.10 (dd, J = 11.2 Hz, 2H), 3.79 (s, 3H), 3.57-3.66 (m, 2H), 3.49-3.57 (m, 1H), 2.50-2.64 (m, 4H), 2.32 (s, 6H), 1.98-2.08 (m, 2H), 1.73 (dd, J = 12.8 Hz, 2H). |
| 3 | 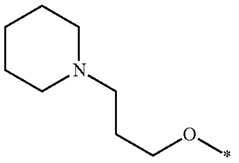 | N | CH | 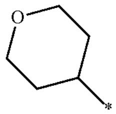 | $CH_3$ | $(M + H)^+$ 502.5 | $CD_3OD$: δ 8.77 (s, 1H), 8.50 (d, J = 2.4 Hz, 1H), 8.39 (s, 1H), 8.07 (dd, J = 2.8 Hz, 8.8 Hz, 1H), 7.98 (d, J = 8.4 Hz, 1H), 7.90 (t, J = 37.2 Hz, 1H), 6.96 (d, J = 8.8 Hz, 1H), 4.40 (t, J = 6.0 Hz, 2H), 4.10 (dd, J = 3.6 Hz, 11.2 Hz, 2H), 3.79 (s, 3H), 3.64-3.58 (m, 3H), 2.60-2.52 (m, 8H), 2.07-2.03 (m, 2H), 1.74 (m, J = 1.6 Hz, 2H), 1.71-1.65 (m, 4H), 1.55-1.45 (m, 2H), 1.29 (s, 1H). |
| 4 | 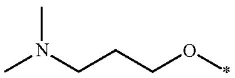 | N | CF | 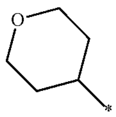 | $CH_3$ | MW 479.55 | / |
| 5 | 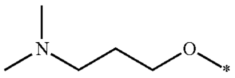 | $CCF_3$ | CH | 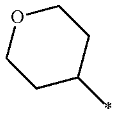 | $CH_3$ | $(M + H)^+$ 529.3 | $CDCl_3$: δ 8.30 (s, 2H), 9.34 (s, 1H), 7.87-7.77 (m, 4H), 7.18 (d, J = 8.4 Hz, 1H), 4.22-4.16 (m, 4H), 3.76 (s, 3H), 3.55 (t, J = 11.6 Hz, 2H), 3.41 (s, 1H), 2.66-2.50 (m, 4H), 2.28 (s, 6H), 2.05-2.01 (m, 2H), 1.74 (s, 1H). |
| 6 | 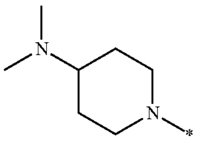 | CF | CH | 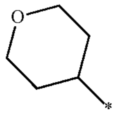 | $CH_3$ | $(M + H)^+$ 504.5 | $CDCl_3$: δ 8.29 (d, J = 5.6 Hz, 2H), 7.86-7.80 (m, 2H), 7.38-7.33 (m, 2H), 7.09 (t, 1H), 4.17 (d, J = 8.4 Hz, 2H), 3.75 (s, 3H), 3.66-3.62 (m, 2H), 3.61-3.58 (m, 1H), 3.45-3.39 (m, 1H), 2.79 (t, 2H), 2.69-2.63 (m, 2H), 2.38 (s, 6H), 1.98 (d, J = 12.0 Hz, 2H), 1.81-1.74 (m, 3H), 1.26 (s, 2H), 0.89-0.84 (m, 1H). |

-continued

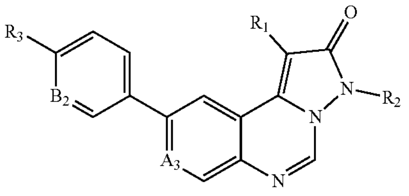

| Example | $R_3$ | $B_2$ | $A_3$ | $R_1$ | $R_2$ | MW/LC-MS (ESI) | $^1$H NMR, 400 MHz |
|---|---|---|---|---|---|---|---|
| 7 | 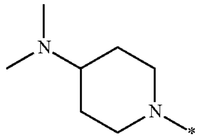 | CCl | CH | 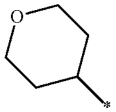 | $CH_3$ | $(M + H)^+$ 520.5 | $CDCl_3$: δ 8.29 (s, 1H), 7.85-7.83 (m, 2H), 7.68 (d, J = 2.0 Hz, 1H), 7.51 (d, J = 8.0 Hz, 1H), 7.17 (d, J = 8.4 Hz, 1H), 4.46 (dd, J = 2.0 Hz, J = 4.4 Hz, 1H), 3.75 (s, 3H), 3.56 (d, J = 12.0 Hz, 4H), 3.46-3.35 (m, 1H), 2.83-2.58 (m, 4H), 2.38 (s, 6H), 1.95 (d, J = 8.4 Hz, 2H), 1.80-1.75 (m, 4H), 1.71 (s, 1H). |
| 8 | 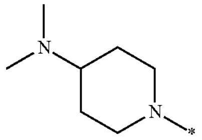 | $CCF_3$ | CH | 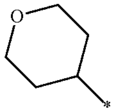 | $CH_3$ | $(M + H)^+$ 554.3 | DMSO-$d_6$: δ 8.81 (s, 1H), 8.35 (s, 1H), 8.08-8.05 (m, 2H), 7.86 (d, J = 2 Hz, 1H), 7.86 (d, J = 2 Hz, 1H), 7.80 (d, J = 8.4 Hz, 1H), 7.66 (d, J = 8.8 Hz, 1H), 3.98 (dd, J = 4.0 Hz, J = 10.8 Hz, 2H), 3.65 (s, 3H), 3.49-3.41 (m, 4H), 3.09 (d, J = 12 Hz, 2H), 2.84-2.79 (m, 2H), 2.50-2.38 (m, 2H), 2.21 (s, 6H), 1.85 (d, J = 12 Hz, 2H), 1.63-1.55 (m, 4H). |
| 9 | 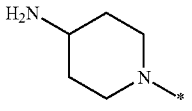 | $CCF_3$ | CH | 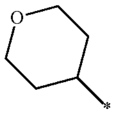 | $CH_3$ | MW 525.58 | / |
| 10 | 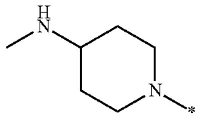 | $CCF_3$ | CH | 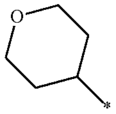 | $CH_3$ | $(M + H)^+$ 540.5 | DMSO-$d_6$: δ 8.81 (s, 1H), 8.35 (s, 1H), 8.08-8.05 (m, 2H), 7.86 (d, J = 2 Hz, 1H), 7.80 (d, J = 8.4 Hz, 1H), 7.66 (d, J = 8.8 Hz, 1H), 3.98 (dd, J = 10.8 Hz, 2H), 3.65 (s, 3H), 3.49-3.41 (m, 3H), 3.30 (s, 1H), 3.09 (d, J = 4.4 Hz, 2H), 2.55 (t, 2H), 2.42-2.38 (m, 2H), 2.30 (s, 6H), 1.85 (d, J = 12 Hz, 2H), 1.63-1.55 (m, 2H), 1.45-1.33 (m, 2H). |
| 11 | 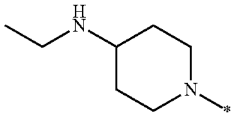 | $CCF_3$ | CH | 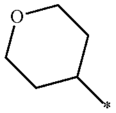 | $CH_3$ | $(M + H)^+$ 554.6 | DMSO-$d_6$: δ 8.80 (s, 1H), 8.34 (s, 1H), 8.05 (s, 1H), 7.97 (s, 1H), 7.86 (d, J = 4.8 Hz, 1H), 7.66-7.64 (m, 1H), 3.97 (d, J = 6.8 Hz, 2H), 3.65 (s, 3H), 3.45-3.43 (m, 3H), 3.06-3.05 (m, 2H), 2.80-2.78 (m, 2H), 2.60-2.58 (m, 3H), 2.42-2.34 (m, 2H), 1.69 (s, 2H), 1.62 (d, J = 11.2 Hz, 2H), 1.42 (d, J = 7.2 Hz, 2H), 1.03 (s, 3H). |
| 12 | 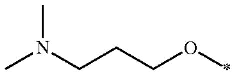 | N | CH | 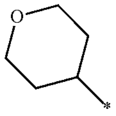 | $CH_3$ | MW 462.55 | / |
| 13 | 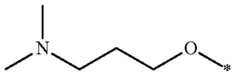 | N | CH | 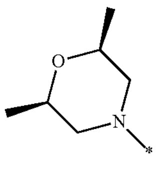 | $CH_3$ | MW 490.6 | / |

-continued
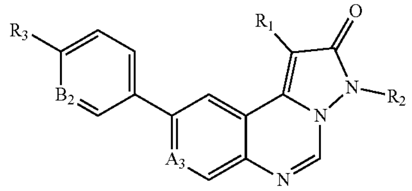
| Example | $R_3$ | $B_2$ | $A_3$ | $R_1$ | $R_2$ | MW/LC-MS (ESI) | $^1$H NMR, 400 MHz |
|---|---|---|---|---|---|---|---|
| 14 | 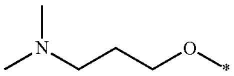 | N | CH | 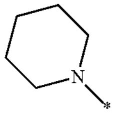 | $CH_3$ | MW 460.58 | / |
| 15 | 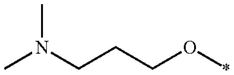 | N | CH | 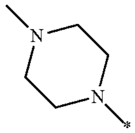 | $CH_3$ | MW 475.60 | / |
| 16 | 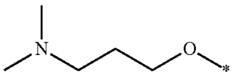 | N | CH | 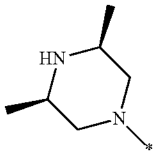 | $CH_3$ | MW 489.62 | / |
| 17 | 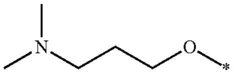 | N | CH | 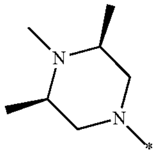 | $CH_3$ | MW 503.65 | / |
| 18 | 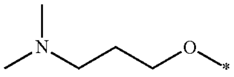 | N | CH | 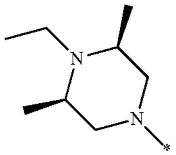 | $CH_3$ | MW 517.68 | / |
| 19 | 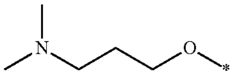 | N | CH | 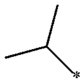 | $CH_3$ | $(M + H)^+$ 420.3 | $CDCl_3$: δ 8.47 (d, J = 2.38 Hz, 1 H), 8.28 (s, 2 H), 7.94-7.75 (m, 3 H), 6.89 (d, J = 8.50 Hz, 1 H), 4.43 (t, J = 6.50 Hz, 2 H), 3.74 (s, 3 H), 3.64-3.52 (m, 1 H), 2.55-2.45 (m, 2 H), 2.29 (s, 6 H), 2.13-1.94 (m, 2 H), 1.52 (d, J = 7.00 Hz, 6 H). |
| 20 | 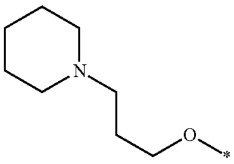 | N | CH | 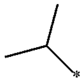 | $CH_3$ | $(M + H)^+$ 460.3 | $CD_3OD$: δ 8.75 (s, 1 H), 8.47 (d, J = 2.45 Hz, 1 H), 8.35 (d, J = 1.71 Hz, 1 H), 8.04 (dd, J = 8.68, 2.57 Hz, 1 H), 7.95 (dd, J = 8.62, 1.77 Hz, 1 H), 7.85 (d, J = 8.56 Hz, 1 H), 6.94 (d, J = 8.56 Hz, 1 H), 4.40 (t, J = 6.24 Hz, 2 H), 3.78 (s, 3 H), 3.69-3.66 (m, 1 H), 2.65-2.46 (m, 6 H), 2.12-2.00 (m, 2 H), 1.68-1.62 (m, 4 H), 1.53-1.51 (m, 8 H). |
| 21 | 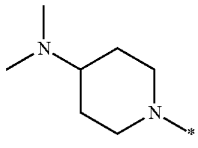 | CF | CH | 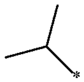 | $CH_3$ | $(M + H)^+$ 462.5 | $CDCl_3$: δ 8.29-8.24 (m, 2H), 7.82-7.78 (m, 2H), 7.38-7.32 (m, 2H), 7.09 (t, 1H), 3.74 (s, 3H), 3.65-3.32 (m, 2H), 3.60-3.55 (m, 1H), 2.79 (t, 2H), 2.41 (s, 6H), 2.03-2.00 (m, 2H), 1.85-1.76 (m, 3H), 1.53 (d, J = 7.2 Hz, 6H). |

-continued

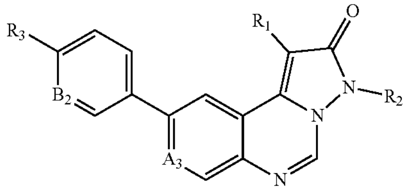

| Example | $R_3$ | $B_2$ | $A_3$ | $R_1$ | $R_2$ | MW/LC-MS (ESI) | $^1$H NMR, 400 MHz |
|---|---|---|---|---|---|---|---|
| 22 | 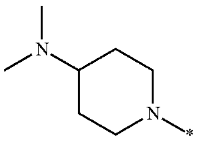 | CCl | CH | 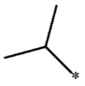 | $CH_3$ | $(M + H)^+$ 478.4 | $CDCl_3$: δ 8.27 (s, 2H), 7.83-7.81 (m, 2H), 7.66 (d, J = 2.0 Hz, 1H), 7.50 (dd, J = 2.0 Hz, 8.4 Hz, 1H), 7.17 (d, J = 9.2 Hz, 1H), 3.74 (s, 3H), 3.59-3.54 (m, 3H), 2.77-2.71 (m, 2H), 2.37 (s, 6H), 2.35-2.38 (m, 1H), 1.98-1.95 (m, 2H), 1.84-1.77 (m, 2H), 1.53 (d, J = 6.8 Hz, 6H). |
| 23 | 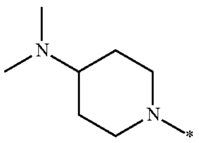 | $CCF_3$ | CH | 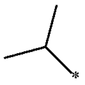 | $CH_3$ | $(M + H)^+$ 512.4 | DMSO-$d_6$: δ 8.29 (d, J = 4.0 Hz, 1H), 7.89 (d, J = 1.6 Hz, 1H), 7.83 (s, 2H), 7.77 (dd, J = 2.0 Hz, J = 8.0 Hz, 1H), 7.46 (d, J = 8.4 Hz, 1H), 3.75 (s, 3H), 3.62-3.57 (m, 1H), 3.24 (d, J = 11.2 Hz, 2H), 2.81 (t, 2H), 2.36 (s, 6H), 2.34-3.32 (m, 2H), 1.92 (d, J = 16.0 Hz, 2H), 1.80-1.62 (m, 2H), 1.53 (d, J = 6.8 Hz, 6H). |
| 24 | 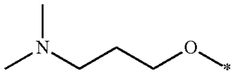 | CF | CH | 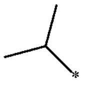 | $CH_3$ | $(M + H)^+$ 437.3 | $CDCl_3$: δ 8.28 (s, 1H), 8.26 (s, 1H), 7.80 (s, 1H), 7.41-7.37 (m, 2H), 7.13 (t, J = 8.6 Hz, 1H), 4.25 (t, J = 5.4 Hz, 2H), 3.74 (s, 3H), 3.61-3.54 (m, 1H), 3.22-3.16 (m, 2H), 2.76 (s, 6H), 2.42-2.40 (m, 2H), 1.55 (s, 3H), 1.53 (s, 3H). |
| 25 | 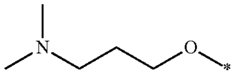 | $CCF_3$ | CH | 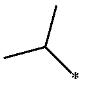 | $CH_3$ | $(M + H)^+$ 487.2 | $CDCl_3$: δ 8.28 (s, 1H), 8.27 (t, J = 0.8 Hz, 1H), 7.85 (d, J = 0.8 Hz, 1H), 7.82 (d, J = 0.4 H, 2H), 7.76 (dd, J = 1.2 Hz, 4.2 Hz, 1H), 7.17 (d, J = 4.2 Hz, 1H), 4.21 (t, J = 6.2 Hz, 2H), 3.75 (s, 3H), 3.57 (t, J = 7.2 Hz, 1H), 2.53 (t, J = 7.2 Hz, 2H), 2.28 (s, 6H), 2.08-2.01 (m, 2H), 1.55 (s, 3H), 1.53 (s, 3H). |
| 26 | 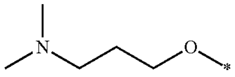 | N | CH | 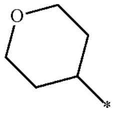 | $CH_2CH_3$ | $(M + H)^+$ 476.5 | $CDCl_3$: δ 8.45 (d, J = 2.4 Hz, 1H), 8.30 (s, 1H), 8.27 (d, J = 1.2 Hz, 1H), 7.87 (d, J = 8.6 Hz, 2.6 Hz, 1H), 7.84 (s, 1H), 7.82 (dd, J = 8.4 Hz, 2.0 Hz, 1H), 6.90 (d, J =8.4 Hz, 1H), 4.46 (t, J = 7.0 Hz, 2H), 4.33 (dd, J = 14.4 Hz, 7.4 Hz, 2H), 4.16 (dd, J = 11.4 Hz, 4.2 Hz, 2H), 3.56 (t, J = 10.8 Hz, 2H), 3.43-3.36 (m, 1H), 2.83-2.77 (m, 1H), 2.67-2.62 (m, 2H), 2.51 (s, 6H), 2.19-2.15 (m, 2H), 1.72-1.69 (m, 3H), 1.38 (t, J = 7.2 Hz, 3H). |
| 27 | 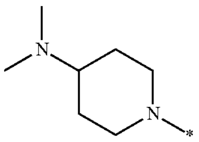 | N | CH | 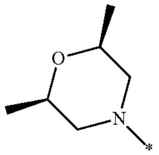 | $CH_3$ | MW 515.65 | / |
| 28 | 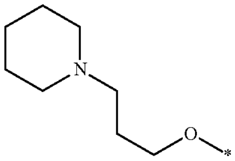 | CF | CH | 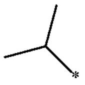 | $CH_3$ | MW 476.59 | / |

Example 29

In Vitro Inhibition of ATM by 9-(6-(3-(dimethylamino)propoxy)pyridin-3-yl)-3-methyl-1-(tetrahydro-2H-pyran-4-yl)pyrazolo[1,5-c]quinazolin-2(3H)-one and its Analogues was Determined by ATM Kinase Assay ATM enzyme activity was measured using HTRF reagents (Cisbio) in a 384-well plate (Greiner, #784075). 2.5 μL of compounds diluted by reaction buffer were added to the corresponding well, then 2.5 μL of 120 nM of p53 substrate (Eurofins, #14-952) and 2.5 μL of 2 ng/μL of ATM enzyme (Eurofins, 14-933) solution were added successively, and finally 2.5 μL of mixed solution (240 μM of ATP, 20 mM of $Mg(AcO)_2$ and 20 mM of $MnCl_2$) were added. The mixture was centrifuged at 1000 rpm for 1 minute, and reacted at room temperature away from light for 30 minutes. Then 5 μL of EDTA stop solution (250 mM) was added to stop the reaction. After 5 μL of detection mixture (Anti-phospho-p53 (ser15)-K (Cisbio, #61P08KAE, 0.084 ng/μL) and Anti-GST-d2 (Cisbio, #61GSTDLA, 5.00 ng/μL)) was finally added to each well, then incubate the plate overnight at room temperature. The fluorescence values at 665 nm and 615 nm were measured on the Envision 2104 instrument. The final reagent concentration was: 12.5 mM HEPES (pH8.0), 0.5% glycerin, 0.005% Brij-35, 0.625 mM DTT, 0.0125% BSA, 15 nM p53, 0.25 ng/μL ATM, 30 μM ATP, 2.5 mM $Mg(AcO)_2$, 2.5 mM $MnCl_2$, 62.5 mM EDTA, 0.021 ng/μL Anti-phospho-p53, 1.25 ng/μL Anti-GST-d2.

Relative fluorescence ratio was calculated: $Ratio_{665\ nm/615\ nm}$-$Ratio_{background}$, and inhibition rate %=(1−(relative fluorescence ratio of test compound well−relative fluorescence ratio of positive control well)/(relative fluorescence ratio of negative control well−relative fluorescence ratio of positive control well))×100 was calculated. Data were analyzed using GraphPad Prism6.0, and fitted using the curve equation: Y=Bottom+(Top−Bottom)/(1+10^((Log $IC_{50}$−X)×HillSlope)) and $IC_{50}$ values were calculated.

Table 1 summarizes the ATM kinase inhibition data of compounds (% inhibition rate).

TABLE 1

| Example | 1 | | | 2 | | | 3 | | | 5 | | | 6 | | |
|---|---|---|---|---|---|---|---|---|---|---|---|---|---|---|---|
| C (μm) | 100 | 10 | 1 | 100 | 10 | 1 | 10 | 1 | 0.1 | 10 | 1 | 0.1 | 10 | 1 | 0.1 |
| Inh (%) | 69 | 23 | 0 | 100 | 96 | 87 | 98 | 93 | 66 | 100 | 93 | 61 | 98 | 94 | 57 |
| Example | 7 | | | 8 | | | 10 | | | 11 | | | 19 | | |
| C (μm) | 10 | 1 | 0.1 | 10 | 1 | 0.1 | 10 | 1 | 0.1 | 10 | 1 | 0.1 | 10 | 1 | 0.1 |
| Inh (%) | 96 | 91 | 61 | 100 | 99 | 86 | 100 | 95 | 87 | 100 | 95 | 66 | 100 | 95 | 74 |
| Example | 20 | | | 21 | | | 22 | | | 23 | | | 24 | | |
| C (μm) | 10 | 1 | 0.1 | 10 | 1 | 0.1 | 10 | 1 | 0.1 | 10 | 1 | 0.1 | | 10 | |
| Inh (%) | 98 | 97 | 71 | 100 | 97 | 60 | 99 | 93 | 51 | 100 | 95 | 26 | | 98 | |
| Example | 25 | | | 26 | | | AZD0156 | | | | | | | | |
| C (μm) | 10 | 1 | 0.1 | | 1 | | 100 | 10 | 1 | | | | | | |
| Inh (%) | 100 | 98 | 35 | | 66.5 | | 100 | 95 | 90 | | | | | | |

Therefore, as determined by ATM kinase assay, 9-(6-(3-(dimethylamino)propoxy)pyridin-3-yl)-3-methyl-1-(tetrahydro-2H-pyran-4-yl)pyrazolo[1,5-c]quinazolin-2(3H)-one (Example 2) and its analogues have a good inhibitory effect on ATM kinase activity.

Example 30

Inhibitory Effects of 9-(6-(3-(dimethylamino)propoxy)pyridin-3-yl)-3-methyl-1-(tetrahydro-2H-pyran-4-yl)pyrazolo[1,5-c]quinazolin-2(3H)-one and its Analogues Combined with CPT-11 on the Growth of Human Colon Cancer Cell SW620 were Determined by MTT Assay The revived SW620 cells were cultured and passaged until they grew well and had a confluence about 90%. SW620 cells were digested by trypsinase, centrifuged at 800 rpm for 5 minutes, the supernatant was discarded, resuspended with fresh medium (RPMI 1640 medium+10% FBS) and counted. The cells were seeded into 96-well cell culture plate with appropriate cell density and incubated overnight in a 37° C. 5% $CO_2$ incubator. The stock solutions of the tested compound and the reference compound AZD0156 were serially diluted to 8 concentrations by DMSO at the ratios of 1:3 and 1:10, respectively, the first concentration was 1 M or 0.333 μM, and the last concentration was negative control of DMSO (0 μM, the final concentration of DMSO was 1‰). 5 μL of each concentration was added to 120 μL of medium (25 times diluted) and mixed by shaking. The overnight cells were taken and the culture medium was removed, 195 μL of fresh medium containing 205 nM CPT-11 was added to each well, and 5 μL of diluted medium containing the corresponding concentration of the tested sample was added respectively, and the culture plate was then placed in the 5% $CO_2$ cell culture incubator at 37° C. for 5 days. After removing the original solution, 100 μL of fresh serum-free DMEM medium containing MTT (0.5 mg/mL) was added to each well, the culture was continued. After 4 hours, the original solution was removed, 100 μL of DMSO was added into each well, the 96-well plates were, shaken away from light for 10 minutes and placed in a multi-function reader to read the absorbance at the wavelength of 552/690 nm. GraphPad Prism 6.0 was used to analyze the data. The inhibitory activity of compounds on cell proliferation was plotted based on cell viability and compound concentration. The $IC_{50}$ value was fitted by a sigmoidal dose response curve equation Y=100/(1+10^(Log C−Log $IC_{50}$)), where C was the concentration of compound.

Table 2 summarizes the inhibitory effects of compounds-combined with CPT-11 on the growth of human colon cancer cell SW620 ($IC_{50}$).

TABLE 2

| Example | 1 | 2 | 3 | 5 | 6 | 7 | 8 | 10 | 11 |
|---|---|---|---|---|---|---|---|---|---|
| $IC_{50}$ (nm) | >1000 | 9.80 | 6.22 | 1.52 | 2.69 | 3.16 | 2.10 | 1.46 | 4.82 |
| Example | 19 | 20 | 21 | 22 | 23 | 24 | 25 | 26 | AZD0156 |
| $IC_{50}$ (nm) | 5.67 | 3.48 | 10.46 | 26.1 | 8.49 | 47.63 | 13.44 | 141.6 | 9.77 |

Therefore, as determined by MTT assay, 9-(6-(3-(dimethylamino)propoxy)pyridin-3-yl)-3-methyl-1-(tetrahydro-2H-pyran-4-yl)pyrazolo[1,5-c]quinazolin-2(3H)-one (Example 2) and its analogues have a good inhibitory effect on the proliferation of SW620 cell.

Example 31

Inhibitory Effects of 9-(6-(3-(dimethylamino)propoxy)pyridin-3-yl)-3-methyl-1-(tetrahydro-2H-pyran-4-yl)pyrazolo[1,5-c]quinazolin-2(3H)-one and its Analogues on the Growth of Human Breast Cancer Cell MDA-MB-468 were Determined by MTT Assay The revived human breast cancer MDA-MB-468 cells were cultured and passaged until they grew well and had a confluence about 90%. MDA-MB-468 cells were digested by trypsinase, centrifuged at 800 rpm for 5 minutes, the supernatant was discarded, resuspended with fresh medium (RPMI 1640 medium+10% FIBS) and counted. The cells were seeded into 96-well cell culture plate with appropriate cell density and incubated overnight in a 37° C. 5% $CO_2$ incubator. The stock solutions of the tested compound and the reference compound AZD0156 were serially diluted to 8 concentrations by DMSO at the ratios of 1:3 and 1:10, respectively: the first concentration was 1 μM or 0.333 μM, and the last concentration was negative control of DMSO (0 μM, the final concentration of DMSO was 1‰). 5 μL of each concentration was added to 120 μL of medium (25 times diluted) and mixed by shaking. The overnight cells were taken and the culture medium was removed, 195 μL of fresh medium was added to each well, and 5 μL of diluted medium containing the corresponding concentration of the tested sample was added, respectively, and the culture plate was then placed in the 5% $CO_2$ cell culture incubator at 37° C. for 7 days (On the fourth day, the medium containing drugs was removed and fresh medium containing drugs was added for continuous cultivation.). After removing the original solution, 100 μL of fresh serum-free DMEM medium containing MTT (0.5 mg/mL) was added to each well, the culture was continued. After 4 hours, the original solution was removed, 100 μL of DMSO was added into each well, the 96-well plates were shaken away from light for 10 minutes and placed in a multi-function reader to read the absorbance at the wavelength of 552/690 nm. GraphPad Prism 6.0 was used to analyze the data. The inhibitory activity of compounds on cell proliferation was plotted based on cell viability and compound concentration. The $IC_{50}$ value was fitted by a sigmoidal dose response curve equation $Y=100/(1+10\hat{}(\text{Log C}-\text{Log IC}_{50}))$, where C was the concentration of compound.

Table 3 summarizes the inhibitory effects of compounds on the growth of human breast cancer cell MDA-MB-468 ($IC_{50}$).

TABLE 3

| Example | 1 | 2 | 3 | 5 | 6 | 7 | 8 | 10 | 11 |
|---|---|---|---|---|---|---|---|---|---|
| $IC_{50}$ (nm) | 231.2 | 9.50 | 6.00 | 2.38 | 2.71 | 3.79 | 2.65 | 2.27 | 3.55 |
| Example | 19 | 20 | 21 | 22 | 23 | 24 | 25 | 26 | AZD0156 |
| $IC_{50}$ (nm) | 5.55 | 2.21 | 7.22 | 22.88 | 6.76 | 43.84 | 13.53 | 123.3 | 9.87 |

Therefore, as determined by MTT assay, 9-(6-(3-(dimethylamino)propoxy)pyridin-3-yl)-3-methyl-1-(tetrahydro-2H-pyran-4-yl)pyrazolo[1,5-c]quinazolin-2(3H)-one (Example 2) and its analogues have a good inhibitory effect on the proliferation of MDA-MB-468 cells.

Having now fully described this disclosure, it will be understood by those of ordinary skill in the art that the same can be performed within a wide and equivalent range of conditions, formulations and other parameters without affecting the scope of the disclosure or any embodiment thereof. All patents, patent applications and publications cited herein are fully incorporated by reference herein in their entirety.

What is claimed is:

1. A compound having the Formula I:

I

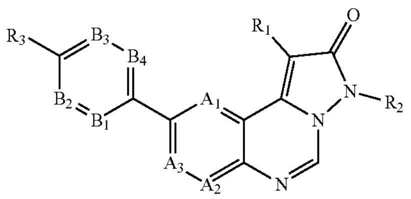

or stereoisomers, tautomers, N-oxides, hydrates, isotope-substituted derivatives, solvates or pharmaceutically acceptable salts thereof, or mixtures thereof, wherein:

$A_1$, $A_2$ and $A_3$ each are $CR_4$, $CR_5$ and $CR_6$, respectively;

$B_1$ is CH, $B_2$ is N, $B_3$ is CH and $B_4$ is CH; or $B_1$ is CH, $B_2$ is $CR_8$, $B_3$ is CH and $B_4$ is CH;

$R_1$ is $C_{1-4}$ alkyl or tetrahydropyranyl, optionally substituted by 1-4 $C_{1-6}$ alkyl groups;

$R^2$ is $C_{1-6}$ alkyl;

$R^3$ is $C_{1-6}$ alkoxy substituted by $—NR_{11}R_{12}$, wherein $R_{11}$ and $R_{12}$ each are independently H or $C_{1-6}$ alkyl, or $R_{11}$ and $R_{12}$ together with the N atom to which they are both bonded links to form an optionally substituted 4-8 membered heterocyclic group; or $R_3$ is piperidinyl substituted by $—NR_{11}R_{12}$, wherein $R_{11}$ and $R_{12}$ each are independently H or $C_{1-6}$ alkyl; and $R_4$, $R_5$, and $R_6$ are H; and $R_8$ is H, halogen, $C_{1-4}$ alkyl, or halo $C_{1-4}$ alkyl;

wherein the compound of Formula I is not 9-(6-(3-(dimethylamino)propoxy)pyridin-3-yl)-3-methyl-1-(tetrahydro-2H-pyran-4-yl)pyrazolo[1,5-c]quinazolin-2(3H)-one.

2. The compound of claim 1, wherein $R_2$ is $C_{1-4}$ alkyl.

3. The compound of claim 1, wherein the compound has Formula IIa or IIb:

IIa

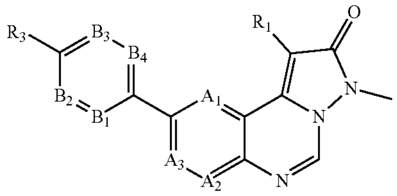

or

IIb

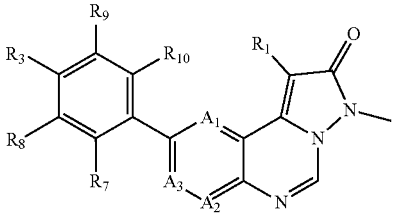

or stereoisomers, tautomers, N-oxides, hydrates, isotope-substituted derivatives, solvates or pharmaceutically acceptable salts thereof, or mixtures thereof, wherein $R_7$, $R_9$, and $R_{10}$ are H.

4. The compound of claim 1, wherein said compound is selected from the group consisting of:

9-(6-(3-(piperidin-1-yl)propoxy)pyridin-3-yl)-3-methyl-1-(tetrahydro-2H-pyran-4-yl)pyrazolo[1,5-c]quinazolin-2(3H)-one;

9-(4-(3-(dimethylamino)propoxy)-3-(trifluoromethyl)phenyl)-3-methyl-1-(tetrahydro-2H-pyran-4-yl)pyrazolo[1,5-c]quinazolin-2(3H)-one;

9-(4-(4-(dimethylamino)piperidin-1-yl)-3-fluorophenyl)-3-methyl-1-(tetrahydro-2H-pyran-4-yl)pyrazolo[1,5-c]quinazolin-2(3H)-one;

9-(3-chloro-4-(4-(dimethylamino)piperidin-1-yl)phenyl)-3-methyl-1-(tetrahydro-2H-pyran-4-yl)pyrazolo[1,5-c]quinazolin-2(3H)-one;

9-(4-(4-(dimethylamino)piperidin-1-yl)-3-(trifluoromethyl)phenyl)-3-methyl-1-(tetrahydro-2H-pyran-4-yl)pyrazolo[1,5-c]quinazolin-2(3H)-one;

9-(4-(4-(methylamino)piperidin-1-yl)-3-(trifluoromethyl)phenyl)-3-methyl-1-(tetrahydro-2H-pyran-4-yl)pyrazolo[1,5-c]quinazolin-2(3H)-one;

9-(4-(4-(ethylamino)piperidin-1-yl)-3-(trifluoromethyl)phenyl)-3-methyl-1-(tetrahydro-2H-pyran-4-yl)pyrazolo[1,5-c]quinazolin-2(3H)-one;

9-(6-(3-(dimethylamino)propoxy)pyridin-3-yl)-1-isopropyl-3-methylpyrazolo[1,5-c]quinazolin-2(3H)-one;

9-(6-(3-(piperidin-1-yl)propoxy)pyridin-3-yl)-1-isopropyl-3-methylpyrazolo[1,5-c]quinazolin-2(3H)-one;

9-(4-(4-(dimethylamino)piperidin-1-yl)-3-fluorophenyl)-1-isopropyl-3-methylpyrazolo[1,5-c]quinazolin-2(3H)-one;

9-(3-chloro-4-(4-(dimethylamino)piperidin-1-yl)phenyl)-1-isopropyl-3-methylpyrazolo[1,5-c]quinazolin-2(3H)-one;

9-(4-(4-(dimethylamino)piperidin-1-yl)-3-(trifluoromethyl)phenyl)-1-isopropyl-3-methylpyrazolo[1,5-c]quinazolin-2(3H)-one;

9-(4-(3-(dimethylamino)propoxy)-3-fluorophenyl)-1-isopropyl-3-methylpyrazolo[1,5-c]quinazolin-2(3H)-one;

9-(4-(3-(dimethylamino)propoxy)-3-(trifluoromethyl)phenyl)-1-isopropyl-3-methylpyrazolo[1,5-c]quinazolin-2(3H)-one; and 9-(6-(3-(dimethylamino)propoxy)pyridin-3-yl)-3-ethyl-1-(tetrahydro-2H-pyran-4-yl)pyrazolo[1,5-c]quinazolin-2(3H)-one;

or stereoisomers, tautomers, N-oxides, hydrates, isotope-substituted derivatives, solvates or pharmaceutically acceptable salts thereof, or mixtures thereof.

5. A pharmaceutical composition comprising a compound of claim 1, or a stereoisomer, a tautomer, a N-oxide, a hydrate, an isotope-substituted derivative, a solvate or a pharmaceutically acceptable salt thereof, or a mixture thereof, and a pharmaceutically acceptable carrier.

6. The pharmaceutical composition of claim 5, wherein the pharmaceutical composition further comprises at least one known anticancer drug, or its pharmaceutically acceptable salts.

7. The pharmaceutical composition of claim 6, wherein the pharmaceutical composition further comprises at least one of the following anticancer drugs: busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, methylhydroxy ellipticine, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, mAb, panitumumab, ofatumumab, avastin, trastuzumab, rituximab, imatinib, gefitinib, erlotinib, lapatinib, sorafinib, sunitinib, nilotinib, dasatinib, pazopanib, bortezomib, torisel, everolimus, vorinostat, romidepsin, tamoxifen, letrozole, fulvestrant, mitoguazone, octreotide, retinoic acid, arsenic trioxide, zoledronic acid, bortezomib, thalidomide, lenalidomide, venetoclax, aldesleukin (recombinant human interleukin-2), sipueucel-T (prostate cancer therapeutic vaccine), palbociclib, olaparib, niraparib, rucaparib, talazoparib or senaparib.

8. The pharmaceutical composition of claim 5, wherein the compound of Formula I has a structure of Formula IIa or IIb:

IIa

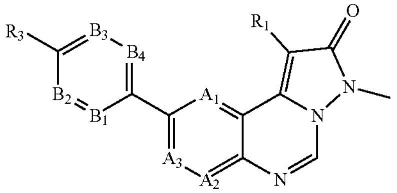

or

IIb

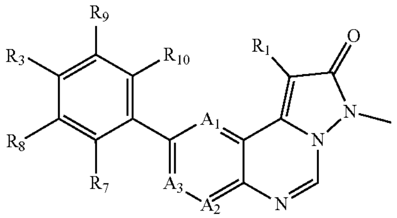

or stereoisomers, tautomers, N-oxides, hydrates, isotope-substituted derivatives, solvates or pharmaceutically acceptable salts thereof, or mixtures thereof, wherein $R_7$, $R_9$, and $R_{10}$ are H.

9. The pharmaceutical composition of claim 5, wherein the compound is selected from the group consisting of:

9-(6-(3-(piperidin-1-yl)propoxy)pyridin-3-yl)-3-methyl-1-(tetrahydro-2H-pyran-4-yl)pyrazolo[1,5-c]quinazolin-2(3H)-one;

9-(4-(3-(dimethylamino)propoxy)-3-(trifluoromethyl)phenyl)-3-methyl-1-(tetrahydro-2H-pyran-4-yl)pyrazolo[1,5-c]quinazolin-2(3H)-one;

9-(4-(4-(dimethylamino)piperidin-1-yl)-3-fluorophenyl)-3-methyl-1-(tetrahydro-2H-pyran-4-yl)pyrazolo[1,5-c]quinazolin-2(3H)-one;

9-(3-chloro-4-(4-(dimethylamino)piperidin-1-yl)phenyl)-3-methyl-1-(tetrahydro-2H-pyran-4-yl)pyrazolo[1,5-c]quinazolin-2(3H)-one;

9-(4-(4-(dimethylamino)piperidin-1-yl)-3-(trifluoromethyl)phenyl)-3-methyl-1-(tetrahydro-2H-pyran-4-yl)pyrazolo[1,5-c]quinazolin-2(3H)-one;

9-(4-(4-(methylamino)piperidin-1-yl)-3-(trifluoromethyl)phenyl)-3-methyl-1-(tetrahydro-2H-pyran-4-yl)pyrazolo[1,5-c]quinazolin-2(3H)-one;

9-(4-(4-(ethylamino)piperidin-1-yl)-3-(trifluoromethyl)phenyl)-3-methyl-1-(tetrahydro-2H-pyran-4-yl)pyrazolo[1,5-c]quinazolin-2(3H)-one;

9-(6-(3-(dimethylamino)propoxy)pyridin-3-yl)-1-isopropyl-3-methylpyrazolo[1,5-c]quinazolin-2(3H)-one;

9-(6-(3-(piperidin-1-yl)propoxy)pyridin-3-yl)-1-isopropyl-3-methylpyrazolo[1,5-c]quinazolin-2(3H)-one;

9-(4-(4-(dimethylamino)piperidin-1-yl)-3-fluorophenyl)-1-isopropyl-3-methylpyrazolo[1,5-c]quinazolin-2(3H)-one;

9-(3-chloro-4-(4-(dimethylamino)piperidin-1-yl)phenyl)-1-isopropyl-3-methylpyrazolo[1,5-c]quinazolin-2(3H)-one;

9-(4-(4-(dimethylamino)piperidin-1-yl)-3-(trifluoromethyl)phenyl)-1-isopropyl-3-methylpyrazolo[1,5-c]quinazolin-2(3H)-one;

9-(4-(3-(dimethylamino)propoxy)-3-fluorophenyl)-1-isopropyl-3-methylpyrazolo[1,5-c]quinazolin-2(3H)-one;

9-(4-(3-(dimethylamino)propoxy)-3-(trifluoromethyl)phenyl)-1-isopropyl-3-methylpyrazolo[1,5-c]quinazolin-2(3H)-one; and 9-(6-(3-(dimethylamino)propoxy)pyridin-3-yl)-3-ethyl-1-(tetrahydro-2H-pyran-4-yl)pyrazolo[1,5-c]quinazolin-2(3H)-one;

or stereoisomers, tautomers, N-oxides, hydrates, isotope-substituted derivatives, solvates or pharmaceutically acceptable salts thereof, or mixtures thereof.

10. A method for treating or disease caused by DDR functional deficiencies or benefiting from the inhibition of kinase activity comprising administering a subject in need thereof an effective amount of a compound of claim 1, or a stereoisomer, a tautomer, a N-oxide, a hydrate, an isotope-substituted derivative, a solvate or a pharmaceutically acceptable salt thereof, or a mixture thereof, or a pharmaceutical composition comprising the compound, or a stereoisomer, a tautomer, a N-oxide, a hydrate, an isotope-substituted derivative, a solvate or a pharmaceutically acceptable salt thereof, or a mixture thereof, and a pharmaceutically acceptable carrier, wherein the pharmaceutical composition optionally further comprises at least one known anticancer drug or its pharmaceutically acceptable salts.

11. The method of claim 10, wherein the disease is cancer.

12. The method of claim 11, wherein the cancer is selected from liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoide, head and neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, b prostatic carcinoma.

13. The method of claim 10, wherein the at least one known anticancer drug is one or more of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, methylhydroxy ellipticine, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, mAb, panitumumab, ofatumumab, avastin, trastuzumab, rituximab, imatinib, gefitinib, erlotinib, lapatinib, sorafinib, sunitinib, nilotinib, dasatinib, pazopanib, bortezomib, torisel, everolimus, vorinostat, romidepsin, tamoxifen, letrozole, fulvestrant, mitoguazone, octreotide, retinoic acid, arsenic trioxide, zoledronic acid, bortezomib, thalidomide, lenalidomide, venetoclax, aldesleukin (recombinant human interleukin-2), sipueucel-T (prostate cancer therapeutic vaccine), palbociclib, olaparib, niraparib, rucaparib, talazoparib or senaparib.

14. The method of claim 13, wherein the subject is treated in combination with radiotherapy.

15. The method of claim 10, wherein the compound is selected from the group consisting of:

9-(6-(3-(piperidin-1-yl)propoxy)pyridin-3-yl)-3-methyl-1-(tetrahydro-2H-pyran-4-yl)pyrazolo[1,5-c]quinazolin-2(3H)-one;

9-(4-(3-(dimethylamino)propoxy)-3-(trifluoromethyl)phenyl)-3-methyl-1-(tetrahydro-2H-pyran-4-yl)pyrazolo[1,5-c]quinazolin-2(3H)-one;

9-(4-(4-(dimethylamino)piperidin-1-yl)-3-fluorophenyl)-3-methyl-1-(tetrahydro-2H-pyran-4-yl)pyrazolo[1,5-c]quinazolin-2(3H)-one;

9-(3-chloro-4-(4-(dimethylamino)piperidin-1-yl)phenyl)-3-methyl-1-(tetrahydro-2H-pyran-4-yl)pyrazolo[1,5-c]quinazolin-2(3H)-one;

9-(4-(4-(dimethylamino)piperidin-1-yl)-3-(trifluoromethyl)phenyl)-3-methyl-1-(tetrahydro-2H-pyran-4-yl)pyrazolo[1,5-c]quinazolin-2(3H)-one;

9-(4-(4-(methylamino)piperidin-1-yl)-3-(trifluoromethyl)phenyl)-3-methyl-1-(tetrahydro-2H-pyran-4-yl)pyrazolo[1,5-c]quinazolin-2(3H)-one;

9-(4-(4-(ethylamino)piperidin-1-yl)-3-(trifluoromethyl)phenyl)-3-methyl-1-(tetrahydro-2H-pyran-4-yl)pyrazolo[1,5-c]quinazolin-2(3H)-one;

9-(6-(3-(dimethylamino)propoxy)pyridin-3-yl)-1-isopropyl-3-methylpyrazolo[1,5-c]quinazolin-2(3H)-one;

9-(6-(3-(piperidin-1-yl)propoxy)pyridin-3-yl)-1-isopropyl-3-methylpyrazolo[1,5-c]quinazolin-2(3H)-one;

9-(4-(4-(dimethylamino)piperidin-1-yl)-3-fluorophenyl)-1-isopropyl-3-methylpyrazolo[1,5-c]quinazolin-2(3H)-one;

9-(3-chloro-4-(4-(dimethylamino)piperidin-1-yl)phenyl)-1-isopropyl-3-methylpyrazolo[1,5-c]quinazolin-2(3H)-one;

9-(4-(4-(dimethylamino)piperidin-1-yl)-3-(trifluoromethyl)phenyl)-1-isopropyl-3-methylpyrazolo[1,5-c]quinazolin-2(3H)-one;

9-(4-(3-(dimethylamino)propoxy)-3-fluorophenyl)-1-isopropyl-3-methylpyrazolo[1,5-c]quinazolin-2(3H)-one;

9-(4-(3-(dimethylamino)propoxy)-3-(trifluoromethyl)phenyl)-1-isopropyl-3-methylpyrazolo[1,5-c]quinazolin-2(3H)-one; and 9-(6-(3-(dimethylamino)propoxy)pyridin-3-yl)-3-ethyl-1-(tetrahydro-2H-pyran-4-yl)pyrazolo[1,5-c]quinazolin-2(3H)-one;

or stereoisomers, tautomers, N-oxides, hydrates, isotope-substituted derivatives, solvates or pharmaceutically acceptable salts thereof, or mixtures thereof.

16. The compound of claim 1, wherein $R_3$ is selected from the group consisting of:

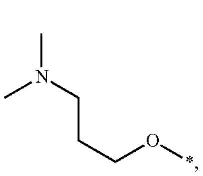,

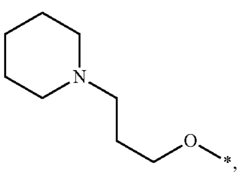,

-continued

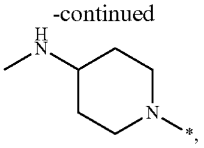,

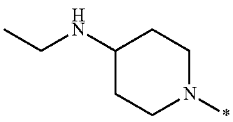 and 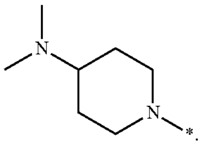.

17. The compound of claim 1, wherein $R_1$ is selected from a group consisting of:

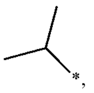, and 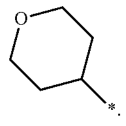.

18. The compound of claim 1, wherein:

$B_2$ is $CR_8$, wherein $R_8$ is halogen or halo $C_{1-4}$ alkyl; $A_3$ is CH; $R_1$ is tetrahydropyranyl or $C_{1-4}$ alkyl; $R_2$ is $C_{1-4}$ alkyl; $R_3$ is $C_{1-6}$ alkoxy substituted by $—NR_{11}R_{12}$, wherein $R_{11}$ and $R_{12}$ each are independently H and $C_{1-4}$ alkyl, or $R_{11}$ and $R_{12}$ together with the N atom to which they are attached form a 4-8 membered heterocyclic group optionally substituted by 1-2 $C_{1-4}$ alkyl; or $B_2$ is $CR_8$, wherein $R_8$ is halogen or halo $C_{1-4}$ alkyl; $A_3$ is CH; $R_1$ is tetrahydropyranyl; $R_2$ is $C_{1-4}$ alkyl; $R_3$ is $C_{1-6}$ alkoxy substituted by $—NR_{11}R_{12}$ or piperidinyl, wherein $R_{11}$ and $R_{12}$ each are independently H or $C_{1-4}$ alkyl; or $B_2$ is $CR_8$, wherein, $R_8$ is halogen or halo $C_{1-4}$ alkyl; $A_3$ is CH, $R_1$ is $C_{1-4}$ alkyl; $R_2$ is $C_{1-4}$ alkyl; $R^3$ is $C_{1-6}$ alkoxy substituted by $—NR_{11}R_{12}$, wherein $R_{11}$ and $R_{12}$ each are independently H or $C_{1-4}$ alkyl, or $R_{11}$ and $R_{12}$ together with the N atom to which they are attached form a 4-8 membered heterocyclic group optionally substituted by 1-2 $C_{1-4}$ alkyl; or $B_2$ is N; $A_3$ is $CR_6$; $R_1$ is $C_{1-4}$ alkyl; $R_2$ is $C_{1-4}$ alkyl; $R_3$ is $C_{1-6}$ alkoxy substituted by $—NR_{11}R_{12}$, wherein $R_6$ is H; $R_{11}$ and $R_{12}$ each are independently H or $C_{1-4}$ alkyl, or $R_{11}$ and $R_{12}$ together with the N atom to which they are attached form a 4-8 membered heterocyclic group optionally substituted by 1-2 $C_{1-4}$ alkyl.

19. The compound of claim 18, wherein the 4-8 membered heterocylic group is piperidinyl.

20. The compound of claim 1, wherein $R_8$ is halogen or halo $C_{1-4}$ alkyl.

* * * * *